US010653560B2

(12) United States Patent
Kakinuma et al.

(10) Patent No.: US 10,653,560 B2
(45) Date of Patent: May 19, 2020

(54) TRANSPARENT LAMINATE

(71) Applicant: DEXERIALS CORPORATION, Shinagawa-ku, Tokyo (JP)

(72) Inventors: Masayasu Kakinuma, Tokyo (JP); Masaki Takenouchi, Tokyo (JP); Eiji Ohta, Tokyo (JP); Satoshi Kawamura, Tokyo (JP); Maki Ogawa, Tokyo (JP)

(73) Assignee: DEXERIALS CORPORATION, Shinagawa-Ku, Tokyo (JP)

(*) Notice: Subject to any disclaimer, the term of this patent is extended or adjusted under 35 U.S.C. 154(b) by 478 days.

(21) Appl. No.: 15/329,779

(22) PCT Filed: Jul. 9, 2015

(86) PCT No.: PCT/JP2015/069710
§ 371 (c)(1),
(2) Date: Jan. 27, 2017

(87) PCT Pub. No.: WO2016/017391
PCT Pub. Date: Feb. 4, 2016

(65) Prior Publication Data
US 2017/0209308 A1    Jul. 27, 2017

(30) Foreign Application Priority Data

Jul. 30, 2014  (JP) ................................ 2014-154450
Mar. 20, 2015  (JP) ................................ 2015-057618

(51) Int. Cl.
*G02B 1/118*    (2015.01)
*A61F 9/02*    (2006.01)
(Continued)

(52) U.S. Cl.
CPC .......... *A61F 9/029* (2013.01); *A41D 13/1184* (2013.01); *A61F 9/02* (2013.01);
(Continued)

(58) Field of Classification Search
CPC ....... G02B 1/118; G02B 27/0006; B32B 3/30; A61F 9/028; A41D 13/1184; A42B 3/22; A42B 3/24
See application file for complete search history.

(56) References Cited

U.S. PATENT DOCUMENTS

| | | | |
|---|---|---|---|
| 5,446,925 A | 9/1995 | Baker et al. | |
| 6,228,499 B1 | 5/2001 | Nakauchi et al. | |
| 10,000,037 B2 * | 6/2018 | Nishimura | ................ B32B 3/30 |
| 2009/0246494 A1 | 10/2009 | Matsumoto | |
| 2010/0323165 A1 | 12/2010 | Sakuma et al. | |

(Continued)

FOREIGN PATENT DOCUMENTS

| | | |
|---|---|---|
| CN | 101663600 A | 3/2010 |
| JP | 5-078507 A | 3/1993 |

(Continued)

OTHER PUBLICATIONS

Office Action issued by the Taiwanese Patent Office in corresponding Taiwanese Patent Application No. 104122787 dated Sep. 12, 2018 (5 pages including partial English translation).

(Continued)

*Primary Examiner* — Tajash D Patel
(74) *Attorney, Agent, or Firm* — Buchanan Ingersoll & Rooney PC

(57) ABSTRACT

A transparent laminate including: transparent substrate; and structure layer which contains protrusion portions, depression portions, or both on a surface thereof, average distance between the protrusion portions adjacent or the depression portions adjacent being equal to or less than wavelength of visible light; the structure layer including polymerized product of active-energy-ray-curable resin composition including composition of (meth)acrylate-based-polymerizable compound; the composition including at least any of the following (A) and (B), and the following (C) and (D): (A) ester (meth)acrylate of trihydric alcohol having main and side chain each including alkyl chain; (B) ester di(meth) acrylate of ethylene-oxide-modified bisphenol A; (C) poly- (Continued)

alkylene glycol di(meth)acrylate; and (D) ester di(meth) acrylate of dihydric alcohol having main chain including linear alkyl chain; water contact angle on the surface of the structure layer being 26° or more and 74° or less; and storage elastic modulus at 180° C. of the structure layer being less than 0.5 GPa.

8 Claims, 12 Drawing Sheets

(51) Int. Cl.
    *B32B 27/30*     (2006.01)
    *C08F 2/46*     (2006.01)
    *B32B 3/30*     (2006.01)
    *C08J 3/24*     (2006.01)
    *G02B 27/00*     (2006.01)
    *G02B 1/18*     (2015.01)
    *C08J 7/04*     (2020.01)
    *A41D 13/11*     (2006.01)

(52) U.S. Cl.
    CPC ............... *B32B 3/30* (2013.01); *B32B 27/30* (2013.01); *C08F 2/46* (2013.01); *C08J 3/24* (2013.01); *C08J 7/0427* (2020.01); *G02B 1/118* (2013.01); *G02B 1/18* (2015.01); *G02B 27/0006* (2013.01); *C08J 2369/00* (2013.01); *C08J 2433/06* (2013.01)

(56) References Cited

U.S. PATENT DOCUMENTS

| | | | |
|---|---|---|---|
| 2012/0147472 A1* | 6/2012 | Kajiya | B32B 3/30 359/601 |
| 2013/0004718 A1 | 1/2013 | Takihara et al. | |
| 2013/0011611 A1 | 1/2013 | Taguchi et al. | |
| 2014/0098422 A1 | 4/2014 | Fukuda et al. | |
| 2015/0355385 A1* | 12/2015 | Horii | G02B 1/105 428/141 |
| 2016/0193808 A1* | 7/2016 | Nishimura | B32B 3/30 |

FOREIGN PATENT DOCUMENTS

| | | |
|---|---|---|
| JP | 7-178117 A | 7/1995 |
| JP | 4796659 B2 | 10/2011 |
| JP | 5042386 B2 | 10/2012 |
| JP | 2013-238808 A | 11/2013 |
| JP | 2014-098864 A | 5/2014 |
| TW | 200831568 A | 8/2008 |
| TW | 201144940 A | 12/2011 |
| WO | WO 96/41831 A1 | 12/1996 |
| WO | WO 2011/115162 A1 | 9/2011 |
| WO | WO 2012/133946 A1 | 10/2012 |

OTHER PUBLICATIONS

International Search Report (PCT/ISA/210) dated Sep. 8, 2015, by the Japanese Patent Office as the International Searching Authority for International Application No. PCT/JP2015/069710.
Written Opinion (PCT/ISA/237) dated Sep. 8, 2015, by the Japanese Patent Office as the International Searching Authority for International Application No. PCT/JP2015/069710.

* cited by examiner (B-B Cross-sectional view)

(A-A Cross-sectional view)

TRANSPARENT LAMINATE

TECHNICAL FIELD

The present invention relates to a transparent laminate.

BACKGROUND ART

A face shield which can protect the face while a visual field is ensured has been conventionally used in order to protect the face from a flying object to the face in a surgery or the like.

For example, a face shield has been proposed which has a structure where a transparent plastic film is attached to a face mask as an eye shield (see, for example, PTL 1).

A surgical lighting system very high in intensity is used in an operating room where a surgery is conducted, and a face shield in such a lighting system is demanded to be a transparent body having high antireflection properties. In addition, mechanical strength such as scratch resistance is also demanded.

As the transparent structure having antireflection properties, a transparent structure is known which has a fine depression and protrusion structure made of a cured product of an active energy ray curable composition (see, for example, PTLs 2 and 3).

PTL 2 discloses a transparent structure where the water contact angle on the surface of a depression and protrusion layer is 25° or less and the elastic modulus of the surface of a depression and protrusion layer is 200 MPa or more to thereby allow the structure to have antifouling properties and abrasion resistance.

In addition, PTL 3 discloses a transparent structure where a polymerizable composition containing 24.8% or more of a tri- or higher functional acrylate compound and 37.2% or more of polyethylene glycol diacrylate is polymerized to form a structure, and the storage elastic modulus at 180° C. or more is 0.5 GPa or more to thereby allow the structure to have antifouling properties and abrasion resistance.

In consideration of putting a face shield or the like to practical use as a medical face protection mask or the like, however, the above-mentioned techniques disclosed cannot be said to be sufficient.

In order to provide a transparent structure suitable for production and use of a medical face protection mask, the transparent structure is required to not only have antifouling properties and abrasion resistance, but also have the following properties: (1) antifogging properties; (2) an enhancement in use selectivity of a surface protection film and (3) prevention of an adverse effect by the surface protection film in use of the surface protection film in production and processing of the medical face protection mask; and (4) crack resistance which causes no cracking in providing a mask shape by punching.

There has not been provided a transparent structure which satisfies all properties including not only antifouling properties and abrasion resistance, but also the above properties (1) to (4), and a transparent structure is demanded which can be put into practical use for a medical face protection mask and the like.

CITATION LIST

Patent Literatures

PTL 1: Japanese Patent Application Laid-Open (JP-A) No. 07-178117

PTL 2: Japanese Patent (JP-B) No. 4796659
PTL 3: JP-B No. 5042386

SUMMARY OF INVENTION

Technical Problem

An object of the present invention is to solve the above conventional problems and to achieve the following object. That is, an object of the present invention is to provide a transparent structure which is excellent in antifouling properties, antifogging properties and abrasion resistance, furthermore, which results in an enhancement in selectivity of a surface protection film for use in production and processing of a medical face protection mask and the like and prevents any adverse effect due to the surface protection film, and which is excellent in crack resistance in providing a mask shape by punching.

Solution to Problem

Solutions for solving the problems are as follows. That is,
<1> A transparent laminate including:
 a transparent substrate; and
 a structure layer,
 wherein the structure layer contains protrusion portions, depression portions, or both on the surface thereof, and an average distance between the protrusion portions adjacent or an average distance between the depression portions adjacent is equal to or less than a wavelength of visible light;
 the structure layer includes a polymerized product of an active energy ray curable resin composition;
 the active energy ray curable resin composition includes a composition of a (meth)acrylate-based polymerizable compound;
 the composition of a (meth)acrylate-based polymerizable compound includes at least any of the following (A) and (B), and the following (C) and (D):
  (A) an ester (meth)acrylate of a trihydric alcohol having a main chain and a side chain each including an alkyl chain;
  (B) an ester di(meth)acrylate of ethylene oxide-modified bisphenol A;
  (C) a polyalkylene glycol di(meth)acrylate; and
  (D) an ester di(meth)acrylate of a dihydric alcohol having a main chain including a linear alkyl chain;
 the water contact angle on the surface of the structure layer is 26° or more and 74° or less; and
 the storage elastic modulus at 180° C. of the structure layer is less than 0.5 GPa.
<2> The transparent laminate according to <1>, wherein the composition of a (meth)acrylate-based polymerizable compound includes the (A), (B), (C) and (D).
<3> The transparent laminate according to <1>, wherein the composition of a (meth)acrylate-based polymerizable compound includes the (A) or the (B), the (C), and the (D), and the water contact angle is 26° or more and 60° or less.
<4> The transparent laminate according to any one of <1> to <3>, wherein the ester (meth)acrylate (A) of a trihydric alcohol having a main chain and a side chain each including an alkyl chain is trimethylolpropane triacrylate.
<5> The transparent laminate according to <4>, wherein the content of the trimethylolpropane triacrylate in the composition of a (meth)acrylate-based polymerizable compound is less than 24.8% by mass.
<6> The transparent laminate according to any one of <1> to <5>, wherein the polyalkylene glycol di(meth)acrylate (C) contains polyethylene glycol diacrylate having more than 8 ethylene oxide (EO) chain repeating units.

<7> The transparent laminate according to any one of <1> to <6>, wherein the tensile elongation at break of the structure layer is 0.65% or more.

<8> The transparent laminate according to any one of <1> to <7>, for use as a face protective optical element.

Advantageous Effects of Invention

The present invention can provide a transparent structure which can solve the conventional various problems and achieve the object, which is excellent in antifouling properties, antifogging properties and abrasion resistance, furthermore which results in an enhancement in selectivity of a surface protection film for use in production and processing of a medical face protection mask and the like and prevents any adverse effect due to the surface protection film, and which is excellent in crack resistance in providing a mask shape by punching.

DESCRIPTION OF EMBODIMENTS (Transparent Laminate)

Figure 1A:
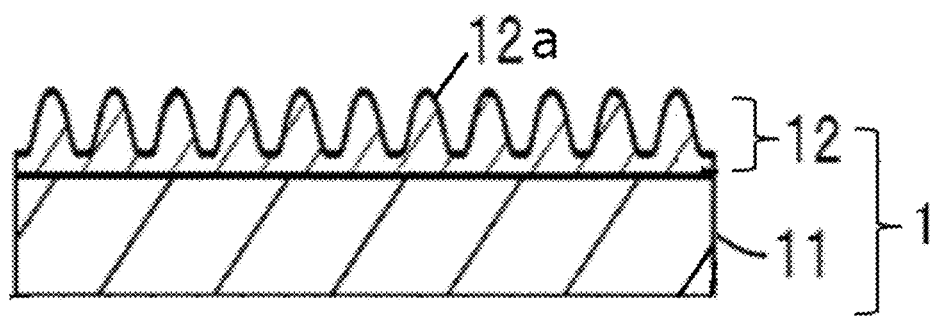
FIG. 1A is a cross-sectional view illustrating one configuration example of the transparent laminate of the present invention.

The transparent laminate of the present invention includes a transparent substrate and a structure layer, and further includes other member, if necessary.

The structure layer contains protrusion portions, depression portions, or both on the surface thereof, and the average distance between the adjacent protrusion portions or the average distance between the adjacent depression portions is equal to or less than a wavelength of visible light.

The structure layer includes a polymerized product of an active energy ray curable resin composition.

The active energy ray curable resin composition includes a composition of a (meth)acrylate-based polymerizable compound.

The composition of a (meth)acrylate-based polymerizable compound includes at least any of the following (A) and (B), and the following (C) and (D):

(A) an ester (meth)acrylate of a trihydric alcohol having a main chain and a side chain each including an alkyl chain;

(B) an ester di(meth)acrylate of ethylene oxide-modified bisphenol A;

(C) a polyalkylene glycol di(meth)acrylate; and
(D) an ester di(meth)acrylate of a dihydric alcohol having a main chain including a linear alkyl chain.

The water contact angle on the surface of the structure layer is 26° or more and 74° or less; and the storage elastic modulus at 180° C. of the structure layer is less than 0.5 GPa.

The present inventors have made studies about a transparent laminate having a fine and dense depression and protrusion (moth-eye; moth's eye) structure on a transparent substrate, as a face protective optical element applicable to a medical face protection mask, thereby leading to the following recognition: it is important for practical use that not only the transparent laminate be excellent in antifouling properties and abrasion resistance, but also the following problems be solved in terms of use as well as production and processing.

Problem 1: when the transparent laminate is used as a medical face protection mask (hereinafter, also referred to as "mask"), the mask surface is prevented from being fogged by the expired breath (enhancement in antifogging properties).

Problem 2: while a surface protection film is used to protect the transparent laminate surface in production and processing of the mask, selectivity of the surface protection film is enhanced to prevent any adverse effect due to the surface protection film.

Problem 3: while the transparent laminate is punched so as to fit to the shape of the mask in production of the mask, such punching is conducted so as not to cause cracking in the transparent laminate (enhancement in crack resistance).

Problem 1 and Problem 2 arise depending on the surface energy of the transparent laminate surface, and the measure of such energy can be represented by the water contact angle. Problem 3 arises depending on the elastic modulus (≈index of hardness) of the transparent laminate.

Problem 1 is based on the constituent material of the transparent laminate, and can be solved by extending the moisture of the expired breath with wetting by use of a material which reduces the water contact angle (imparts hydrophilicity) to thereby impart defogging action. On the other hand, when the material has hydrophilicity, however, the surface protection film is too closely attached to the transparent laminate surface to cause a pressure-sensitive adhesive of the surface protection film to remain in the depression and protrusion portions of the transparent laminate surface, and/or to cause the peeling force to be increased in peeling of the surface protection film, thereby sometimes causing fine depression and protrusion of the transparent laminate surface to be broken, with respect to Problem 2. Thus, optical properties, antifouling properties, antifogging properties and the like are adversely affected.

With respect to Problem 3, while a structure layer is pasted onto a resin substrate having flexibility and is punched together with the resin substrate into the mask shape in production of the mask, the structure layer has so high elastic modulus that the transparent laminate is cracked in such punching, leading to the occurrence of a defective product.

In other words, in consideration of putting the mask into practical use, the water contact angle does not only have to be lower (the mask does not have only to have hydrophilicity) and it is necessary to consider not only antifouling properties and antifogging properties, but also close attachment properties to the surface protection film, and the like, and furthermore, the elastic modulus does not only have to be higher and it is necessary to consider not only scratch resistance, but also crack resistance. Furthermore, the above properties are affected by not only the values of physical properties such as the water contact angle and the elastic modulus, but also the constituent component of the transparent laminate, and therefore comprehensive determination is required.

The present inventors have made intensive studies about the composition of constituent material of the transparent laminate and properties exhibited by the transparent laminate, and as a result, have found that a transparent laminate which includes an active energy ray curable resin composition including a specific component and which exhibits predetermined values of the water contact angle and the elastic modulus exhibits good result with respect to all the items recited in the above problems: antifouling properties, antifogging properties and abrasion resistance; an enhancement in selectivity of the surface protection film and prevention of any adverse effect due to the surface protection film; and crack resistance; in a well-balanced manner.

The ranges of the values of the water contact angle and the elastic modulus determined in the present invention are different from the ranges disclosed in PTLs 1 and 2 above, and the present inventors have found that a transparent laminate exhibiting properties in different ranges from the technical ranges disclosed corresponds to an optical aspect in consideration of practical use to a medical face protection mask and the like.

One example of a cross-sectional view of the configuration of the transparent laminate of the present invention is illustrated in FIGS. 1A and B. As illustrated in FIGS. 1A and B, this transparent laminate 1 has a fine depression and protrusion structure (hereinafter, also referred to as "moth-eye structure") whose size is equal or less than visible wavelengths from several tens nm to several hundreds nm, on the surface thereof.

The transparent laminate 1 includes a transparent substrate 11, and a structure layer 12 having a plurality of structures 12a including protrusion portions or depression portions at an interval equal to or less than a wavelength of visible light (360 nm to 830 nm) on the surface thereof.

Figure 2A:
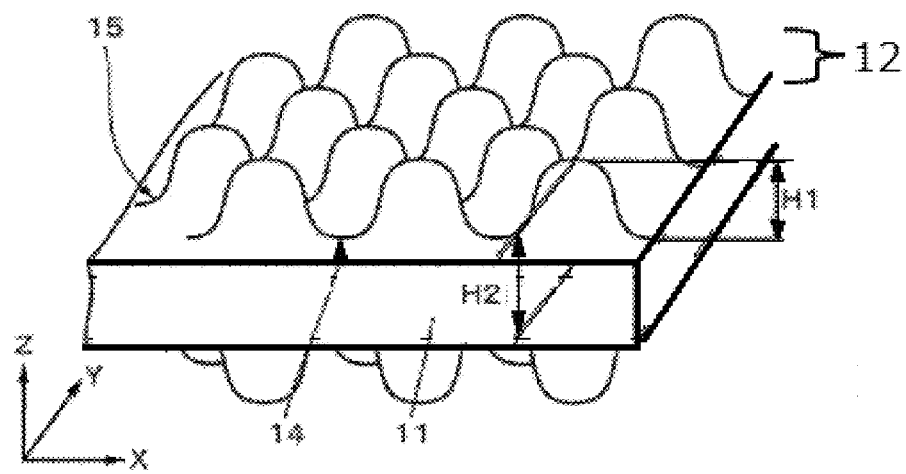
FIG. 2A is a perspective view illustrating one example of the surface shape of the transparent laminate of the present invention.
Figure 2B:
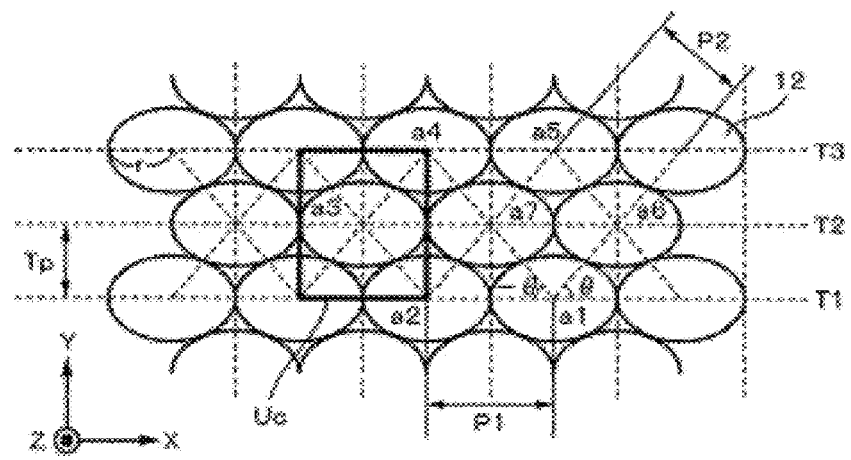
FIG. 2B is a plan view illustrating one example of arrangement of a plurality of protrusion portions formed on the surface of the transparent laminate of the present invention.

While protrusion or depression structures 12a are formed on the surface of the structure layer 12, the plurality of structures 12a are arranged so as to form a plurality of rows. FIG. 2A illustrates one example of a perspective view of the transparent laminate of the present invention, the transparent laminate including a protrusion structure layer 12 on the surface thereof. In addition, FIG. 2B illustrates one example of a plan view of the arrangement of a plurality of protrusion portions formed on the surface.

Figure 1B:
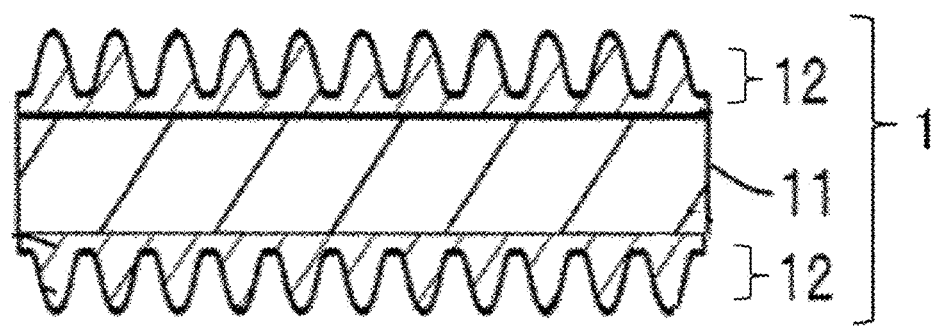
FIG. 1B is a cross-sectional view illustrating another configuration example of the transparent laminate of the present invention.

The transparent laminate of the present invention may include a structure layer 12 where fine depression and protrusion structures 12a are formed, on both front and rear surfaces of the transparent substrate 11 (FIG. 1B).

A transparent laminate including fine and dense depression and protrusion on each of both surfaces thereof can effectively suppress reflection at the interface between the transparent laminate and air. The transparent laminate can be said to be a preferable aspect because of being excellent in visibility such as permeation properties and reflection properties.

The transparent laminate 1 has, for example, transparency to visible light, and the refractive index n thereof is preferably 1.40 or more and 2.00 or less, more preferably 1.43 or more and 2.00 or less. In addition, the transmittance to light at a wavelength of 550 nm is preferably 98.5% or more.

The refractive index of the structure layer 12 is preferably the same or almost the same as the refractive index of the transparent substrate 11. The reason for this is because internal reflection can be suppressed to result in an enhancement in contrast.

<Transparent Substrate>

The material of the transparent substrate is not particularly limited and can be appropriately selected for any purpose, and examples thereof include one mainly including a plastic material, glass or the like having transparency.

Examples of the glass include soda lime glass, lead glass, hard glass, quartz glass and liquid crystallized glass (see "Chemical Handbook" (basic version) P.I-537, edited by the Chemical Society of Japan).

Examples of the plastic material include (meth)acrylic resins such as polymethyl methacrylate, and a copolymer of methyl methacrylate and a vinyl monomer such as other alkyl (meth)acrylate or styrene; polycarbonate-based resins such as polycarbonate and diethylene glycol bis(allyl carbonate) (CR-39); thermosetting (meth)acrylic resins such as a homopolymer and a copolymer of (brominated) bisphenol A di(meth)acrylate, and a polymer and a copolymer of a urethane-modified monomer of (brominated) bisphenol A mono(meth)acrylate; polyesters, in particular, polyethylene terephthalate, polyethylene naphthalate and unsaturated polyester, an acrylonitrile-styrene copolymer, polyvinyl chloride, polyurethane, an epoxy resin, polyallylate, polyether sulfone, polyether ketone, a cycloolefin polymer (trade name: ARTON, ZEONOR), and a cycloolefin copolymer, in terms of optical properties such as transparency, refractive index and dispersion, and also various properties such as impact resistance, heat resistance and durability. An aramid-based resin can also be used in consideration of heat resistance. Here, (meth)acrylate means acrylate or methacrylate. In addition, a (meth)acrylic resin means an acrylic resin or a methacrylic resin.

As the transparent substrate, a resin substrate having flexibility is preferably used. In particular, a transparent laminate where a flexible transparent substrate is used can be preferably applied as a face protective optical element to a medical face protection mask.

When the structure layer 12 and the transparent substrate 11 are separately molded and a plastic material is used for the transparent substrate 11, a primer layer may be provided by a surface treatment in order to more improve the surface energy, coatability, flatness and the like of the plastic surface. Examples of the primer layer include an organoalkoxymetal compound, polyester, acrylic-modified polyester and polyurethane. In order to achieve the same effect as in providing of the primer layer, the surface of the transparent substrate 11 may be subjected to a corona discharge treatment, an UV irradiation treatment or the like.

When the structure layer 12 and the transparent substrate 11 are separately molded and the transparent substrate 11 is a plastic film, the transparent substrate 11 can be obtained by, for example, a method where the above resin is stretched or diluted with a solvent and thereafter formed into a film, and the film is dried.

The average thickness of the transparent substrate 11 can be appropriately selected depending on the application of the transparent laminate 1, and is, for example, preferably 10 μm or more and 500 μm or less, more preferably 50 μm or more and 500 μm or less, particularly preferably 50 μm or more and 300 μm or less. The reason is because an average thickness of 10 μm or more allows protection performance from a flying object to be enhanced, for example, in the case of use as a face protective optical element. On the other hand, the reason is because an average thickness of 500 μm or less can allow for a reduction in weight and also can impart flexibility to thereby allow for deformation into a curved surface shape, resulting in an enhancement in wearing feel as a protection member.

The shape of the transparent substrate is not particularly limited and can be appropriately selected for any purpose, and examples thereof can include a film shape and a plate shape. The film shape here encompasses a sheet shape.

<Structure Layer>

The structure layer contains protrusion portions, depression portions, or both on the surface thereof, and the average distance between the adjacent protrusion portions or the average distance between the adjacent depression portions is equal to or less than a wavelength of visible light.

The structure layer contains a polymerized product of an active energy ray curable resin composition.

The average thickness L (μm) of the structure layer is not particularly limited, can be appropriately selected for any purpose, and is preferably 0.8 μm to 10 μm, more preferably 1 μm to 4 μm.

The average thickness L can be calculated by measuring each of the total thickness of the transparent laminate and the thickness of the transparent substrate ten times by use of a thickness gauge (Litematic VL-50S-B manufactured by Mitutoyo Corporation) to determine the respective average thicknesses, and subtracting the average thickness of the transparent substrate from the average thickness of the transparent laminate.

<<Protrusion Portions and Depression Portions>>

As illustrated in FIG. 2B, a plurality of structures 12a are two-dimensionally arranged on the surface of the structure layer 12 formed on the transparent substrate 11. The structures 12a are preferably periodically two-dimensionally arranged at a short interval (average arrangement pitch) equal to or less than the wavelength band of light for the purpose of a reduction in reflection or an enhancement in permeation.

In the present invention, the interval (pitch) refers to the distance between adjacent protrusion portions, or the distance between adjacent depression portions.

The plurality of structures 12a have an arrangement form where a plurality of rows of tracks T1, T2, T3, . . . (hereinafter, also collectively referred to as "track T".) are present on the surface of the structure layer 12. In the present invention, the track refers to a portion where the plurality of structures 12a are continuously put in rows. As the shape of the track T, a linear or arcuate shape can be used, and a track T having such a shape may be wobbled (serpentine). The track T can be thus wobbled to thereby suppress the occurrence of variation in appearance.

When the track T is wobbled, each wobble of the track T is preferably synchronized. That is, each wobble is preferably a synchronized wobble. Each wobble can be thus synchronized to thereby retain a unit lattice shape of a hexagonal lattice or a quasi-hexagonal lattice, allowing a high filling rate to be kept. Examples of a waveform of the track T wobbled can include a sine wave and a triangle wave. The waveform of the track T wobbled is not limited to a periodic waveform, and may be a non-periodic waveform. The wobble amplitude of the track T wobbled is selected as, for example, about 10 nm to 1 μm.

The structures 12a are arranged, for example, at positions displaced by a half-pitch between two adjacent tracks T. Specifically, structures 12a on one track (for example, T2) are arranged at intermediate positions (positions displaced by a half-pitch) of structures 12a arranged on other track (for example, T1), between two adjacent tracks T. As a result, as illustrated in FIG. 2B, the structures 12a are arranged so that a hexagonal lattice pattern or a quasi-hexagonal lattice pattern is formed where the centers of the structures 12a are positioned at respective points of a1 to a7 among three adjacent rows of tracks (T1 to T3).

The hexagonal lattice here refers to a regular hexagonal lattice. The quasi-hexagonal lattice here refers to a distorted regular hexagonal lattice different from a regular hexagonal lattice. For example, when the structures 12a are linearly arranged, the quasi-hexagonal lattice refers to a hexagonal lattice obtained by stretching and distorting a regular hexagonal lattice in a linear arrangement direction (track direction). When the structures 12a are arranged in an arcuate manner, the quasi-hexagonal lattice refers to a hexagonal lattice obtained by distorting a regular hexagonal lattice in an arcuate manner, or a hexagonal lattice obtained by stretching and distorting a regular hexagonal lattice in an arrangement direction (track direction), and distorting it in an arcuate manner. When the structures 12a are arranged in a serpentine manner, the quasi-hexagonal lattice refers to a hexagonal lattice obtained by distorting a regular hexagonal lattice by serpentine arrangement of the structures 12a, or a hexagonal lattice obtained by stretching and distorting a regular hexagonal lattice in an arrangement direction (track direction), and distorting it by serpentine arrangement of the structures 12a.

When the structures 12a are arranged so as to form a quasi-hexagonal lattice pattern, the arrangement pitch P1 (for example, distance from a1 to a2) of structures 12a in the identical track (for example, T1) is preferably longer than the arrangement pitch of structures 12a between two adjacent tracks (for example, T1 and T2), namely, the arrangement pitch P2 (for example, distance from a1 to a7, distance from a2 to a7) of structures 12a in a ±θ direction to the track extending direction, as illustrated in FIG. 2B. The structures 12a can be thus arranged to thereby result in a further enhancement in the filling density of the structures 12a.

Examples of specific shapes of the structures 12a include cone, column, needle, hemisphere, semioval and polygonal shapes, but are not limited to these shapes, and other shape may be adopted. Examples of the cone shape include a cone shape whose top portion is acuate, a cone shape whose top portion is flat, and a cone shape having a protrusion or depression curved surface on the top portion, but are not limited to these shapes. Examples of the cone shape having a protrusion or depression curved surface on the top portion include a two-dimensionally curved surface shape such as a paraboloid shape. A conical surface may be curved so as to have a depression or protrusion. When a roll master is produced using a roll master exposure apparatus (see FIG. 4) described later, it is preferable that an elliptical cone shape having a protrusion curved surface on the top portion, or an elliptical frustum shape whose top portion is flat be adopted as the shape of each structure 12a, and the longitudinal direction of the elliptical shape forming the bottom surface be consistent with the track T extending direction. The shapes such as elliptical, spherical and ellipsoidal shapes here encompass not only shapes such as complete elliptical, spherical and ellipsoidal shapes mathematically defined, but also shapes such as elliptical, spherical and ellipsoidal shapes to which more or less distortion is provided. The flat shape is not limited to an elliptical shape and the like, and may be a round shape.

A cone shape where the slope of the top portion is gentle and gradually more precipitous from the center portion to the bottom portion is preferable from the viewpoint of an enhancement in optical adjustment function. In addition, a cone shape where the slope of the center portion is more precipitous than those of the bottom portion and the top portion, or a cone shape whose top portion is flat is preferable from the viewpoint of an enhancement in optical adjustment function. When each structure 12a has an elliptical cone shape or an elliptical frustum shape, the longitudinal direction of the bottom surface is preferably parallel with the track extending direction.

Each structure 12a preferably has, on the periphery of the bottom portion thereof, a curved surface portion 15 whose height is gently decreased from the top portion towards the lower portion. The reason is because the transparent laminate 1 can be easily peeled from the master and the like in the production process of the transparent laminate 1. While the curved surface portion 15 may be here provided on only a part of the periphery of each structure 12a, it is preferably provided on all the periphery of each structure 12a in terms of the above peeling properties.

A projection 14 is preferably provided on a part or all the circumference of each structure 12a. Thus, the reflection rate can be kept low even when the filling rate of the structures 12a is low. The projection 14 is preferably provided between any adjacent structures 12a from the viewpoint of ease of molding. The surface of a part of or all the circumference of each structure 12a may also be roughened to form fine depression and protrusion. Specifically, for example, the surface between any adjacent structures 12a may also be roughened to form fine depression and protrusion. A minute hole may also be formed on the surface of each structure 12a, for example, on the top portion thereof.

In FIG. 1A, FIG. 1B, FIG. 2A and FIG. 2B, while the structures 12a have the same size, shape and height, the configuration of the structures 12a is not limited thereto, and structures 12a having two or more sizes, shapes and heights may be formed on the substrate surface.

The height H1 of each structure 12a in the extending direction (X direction) of the track is preferably less than the height H2 of each structure 12a in the arrangement direction (Y direction) of the track. That is, the heights H1 and H2 of such structures 12a preferably satisfy a relationship of H1<H2. The reason is because, if such structures 12a are arranged so that a relationship of H1 H2 is satisfied, the arrangement pitch P1 in the track extending direction is required to be long, thereby resulting in a reduction in filling rate of the structures 12a in the track extending direction. If the filling rate is thus reduced, deterioration in optical adjustment function is caused.

Herein, the heights H1 and H2 of such structures 12a are not limited to a case where all the heights are the same, and such structures 12a may also be configured so as to have a certain height distribution. Structures 12a having such a height distribution can be provided to thereby result in a reduction in wavelength dependency of the optical adjustment function. Accordingly, a transparent laminate 1 having an excellent optical adjustment function can be realized.

The height distribution here means that structures 12a having two or more heights are formed on the surface of the structure layer. For example, a structure 12a having a standard height and a structure 12a having a height different from the standard height of the above structure 12a may be formed. In such a case, the structure 12a having a height different from the standard height is provided, for example, periodically or non-periodically (randomly) on the surface of the structure layer 12. Examples of the periodical direction include the extending direction and the row direction of the track.

The average aspect ratio (the average height of the protrusion portions/the average distance between the adjacent protrusion portions) of the protrusion portions or the average aspect ratio (the average depth of the depression portions/the average distance between the adjacent depression portions) of the depression portions, of the structures 12a provided on the surface of the structure layer 12, is not particularly limited, can be appropriately selected for any purpose, and is preferably 0.66 to 1.96, more preferably 0.76 to 1.96. When the average aspect ratio is 0.66 or more, low-reflection properties can be enhanced. On the other hand, when the average aspect ratio is 1.96 or less, releasability and the like can be enhanced.

The average arrangement pitch P (referred to as the average distance between adjacent protrusion portions, or the average distance between adjacent depression portions) of the structures 12a is preferably equal to or less than the wavelength band of light for the purpose of an optical adjustment function. The wavelength band of light for the purpose of an optical adjustment function, in the present invention, refers to, for example, the band equal to or less than the wavelength band of visible light (wavelength band from 360 nm to 830 nm).

The average height H of the protrusion portions or the average depth H of the depression portions of the structures 12a is not particularly limited, can be appropriately selected for any purpose, and is preferably 100 nm to 300 nm, more preferably 190 nm to 300 nm, further preferably 180 nm to 230 nm. When the average height H of the protrusion portions or the average depth H of the depression portions of the structures 12a, is 100 nm or more, low-reflection properties can be enhanced. On the other hand, when the average height H of the protrusion portions or the average depth H of the depression portions of the structures 12a is 300 nm or less, releasability and the like can be enhanced.

The average arrangement pitch (average distance (Pm)) of the protrusion portions or depression portions, and the average height of the protrusion portions or the average depth (Hm) of the depression portions can be measured as follows.

[Measurement of Pm (nm) and Hm (nm)]

First, the surface S of the structure layer having protrusion portions or depression portions is observed by an atomic force microscope (AFM), and the pitch between protrusion portions or depression portions, and the height of each protrusion portion or the depth of each depression portion are determined from the cross-section profile of AFM. Such operations are repeatedly conducted at 10 points randomly selected on the surface of the structure layer, and pitches $P(1), P(2), \ldots, P(10)$ and heights or depths $H(1), H(2), \ldots, H(10)$ are determined.

The pitch between protrusion portions means the distance between the vertices of the protrusion portions. The pitch between depression portions means the distance between the deepest parts of the depression portions. The height of each protrusion portion refers to the height of each protrusion portion with the minimum point of a trough between protrusion portions being defined as a standard. The depth of each depression portion refers to the depth of each depression portion with the maximum point of a peak between depression portions being define as a standard.

Next, such pitches $P(1), P(2), \ldots, P(10)$ and heights or depths $H(1), H(2), \ldots, H(10)$ are simply averaged out (arithmetically averaged out) to provide the average distance (Pm) between protrusion portions or depression portions and the average height of the protrusion portions or the average depth (Hm) of the depression portions, respectively.

In the AFM observation, in order that the vertex of protrusion or the bottom side of depression of the cross-section profile is consistent with the vertex of a protrusion portion or the deepest part of a depression portion of a stereoscopic shape, the cross-section profile is obtained by cutting out so as to allow the cross-section to pass through the vertex of protrusion portions of a stereoscopic shape to be measured or the deepest part of a depression portion of a stereoscopic shape.

When the structures 12a have an anisotropic shape (for example, elliptical cone shape or elliptical frustum shape), respective pitches $P(1), P(2), \ldots, P(10)$ can also be determined as follows.

With respect to the respective pitches P1 and P2 represented in FIG. 2B, the pitch $P(1)$ may be determined according to the following expression (1), each of $P(2), \ldots, P(10)$ may be determined in the same manner, and the average of pitches $P(1), P(2), \ldots, P(10)$ at 10 points randomly selected may be taken to provide the average arrangement pitch (Pm).

$$\text{Pitch } P=(P1+P2+P2)/3 \qquad (1)$$

Provided that P1 represents the arrangement pitch in the track extending direction (periodicity in the track extending direction); and P2 represents the arrangement pitch of structures between adjacent tracks. Herein, the arrangement direction θ of structures between tracks to the track extending direction is represented by θ=60°−δ, and δ preferably satisfies 0°<δ≤11°, more preferably 3°≤δ≤6°.

The height of each structure 12a corresponds to the height in the direction (Y direction) between tracks. Since the height H1 of each structure 12a in the track extending direction (X direction) is usually less than the height in the direction (Y direction) between tracks and the height of each structure 12a in an area other than the track extending direction is usually almost the same as the height in the direction between tracks, the height of each structure 12a is typified by the height in the direction between tracks in the present invention, unless otherwise noted. When each structure 12a corresponds to a depression portion, the height (Hm) of the structure 12a is assumed to be the depth (Hm) of each structure 12a.

When the arrangement of the structures 12a forms a hexagonal lattice pattern or a quasi-hexagonal lattice pattern, and the arrangement pitch of structures 12a in the track extending direction is designated as P1 and the arrangement pitch of structures 12a between adjacent tracks is designated as P2 (see FIG. 2B), the ratio P1/P2 preferably satisfies a relationship of 1.00≤P1/P2≤1.1. Such a numerical range can enhance the filling rate of structures 12a having an elliptical cone or elliptical frustum shape, and therefore can enhance the optical adjustment function.

The filling rate of the structures 12a on the surface of the structure layer 12 is 40% or more, preferably 65% or more, more preferably 73% or more, and further preferably 86% or more, with the upper limit thereof being 100%. The filling rate can be within such a range to result in an enhancement in antireflection properties. In order to enhance the filling rate, it is preferable that the lower portions of adjacent structures 12a be jointed or the ellipticity of the bottom surface of each structure 12a be adjusted or the like to impart distortion to each structure 12a.

The filling rate (average filling rate) of the structures 12a is a value determined as follows.

First, the surface of the transparent laminate 1 is photographed using a scanning electron microscope (SEM) by Top View. Next, any unit lattice Uc is randomly selected from the SEM photograph taken, and the arrangement pitch P1 and the track pitch Tp of the unit lattice Uc are measured (see FIG. 2B). In addition, the area S of the bottom surface of a structure 12a positioned at the center of the unit lattice Uc is measured by image processing. Next, the arrangement pitch P1, the track pitch Tp and the area S of the bottom surface measured are used to determine the filling rate according to the following expression (2).

$$\text{Filling rate} = (S(\text{hex.})/S(\text{unit})) \times 100 \quad (2)$$

Provided that when the arrangement of the structures 12a forms a hexagonal lattice pattern or a quasi-hexagonal lattice pattern, the unit lattice area satisfies S (unit)=P1×2Tp The area of the bottom surface of a structure 12a present in the unit lattice satisfies S (hex.)=2S The processing for calculation of the filling rate is performed with respect to unit lattices at 10 points randomly selected from the SEM photograph taken. The measurement values are simply averaged out (arithmetically averaged out) to provide the average of the filling rate, and the resultant average is defined as the filling rate of the structures 12a on the transparent laminate surface.

When the structures 12a are overlapped and/or a co-structure such as a projection 14 is present between the structures 12a, the filling rate can be determined by a method where a part whose height corresponds to 5% relative to the height of each structure 12a is defined as the threshold value and the area ratio is determined.

The structures 12a are preferably connected so that the lower portions thereof are overlapped. Specifically, the lower portions of a part or all of any adjacent structures 12a are preferably overlapped, and are preferably overlapped in the track direction, the θ direction or both the directions. The lower portions of the structures 12a can be thus overlapped to thereby enhance the filling rate of the structures 12a. The structures 12a are preferably overlapped at a portion corresponding to quarter or less of the maximum of the wavelength of light under a usage environment. The reason is because an excellent optical adjustment function can be thus achieved.

The ratio ((2r/P1)×100) of the radius 2r of the structure bottom surface to the arrangement pitch P1 is preferably 85% or more, more preferably 90% or more, further preferably 95% or more. The reason is because such a range can enhance the filling rate of the structures 12a to result in an enhancement in optical adjustment function. If the ratio ((2r/P1)×100) is increased to too largely overlap the structures 12a, the optical adjustment function tends to be deteriorated. Accordingly, the upper limit of the ratio ((2r/P1)× 100) is preferably set so that the structures 12a are jointed at an optical path length in consideration of the refractive index and at a portion corresponding to quarter or less of the maximum of the wavelength of light under a usage environment. Here, the arrangement pitch P1 corresponds to the arrangement pitch of the structures 12a in the track extending direction (X direction), and the radius 2r corresponds to the radius of the bottom surface of each structure 12a in the track extending direction (X direction). When the bottom surface of each structure 12a has a round shape, the radius 2r corresponds to a diameter, and when the bottom surface of each structure 12a has an elliptical shape, the radius 2r corresponds to a longer diameter.

When the structures 12a forms a quasi-hexagonal lattice pattern, the ellipticity e of the bottom surface of each structure 12a preferably satisfies 100%<e<150% or less. The reason is because the ellipticity e can be within such a range to thereby enhance the filling rate of the structures 12a, providing an excellent optical adjustment function.

The transparent substrate 11 has an average thickness appropriately selected depending on the application of the transparent laminate 1 and preferably has flexibility and rigidity depending on the application, and may be, for example, formed so as to have an average thickness within the above range.

In addition, while the structure layer 12 is formed with having a proper average thickness depending on the application or whether the structure layer 12 is formed on one surface or both surfaces of the transparent substrate, the structure layer 12 may be, for example, formed within the above range. When the structure layer 12 is formed on the both surfaces, the average thicknesses of the structure layers on the both surfaces are not necessarily the same.

When the structure layer 12 is formed on both surfaces of the transparent substrate, and the height of each structure 12a of a structure layer 12 formed on one surface of the transparent substrate 11 is designated as Ha, the average thickness of the transparent substrate 11 is designated as T and the height of each structure 12a of a structure layer 12 formed on other surface of the transparent substrate 11 (a surface opposite to the surface on which the structure layer having the height Ha is provided) is designated as Hb, Ha:T:Hb preferably satisfies 18 to 30:800 to 300000:18 to 30 and Ha:T:Hb more preferably satisfies 18 to 30:1000 to 50000:18 to 30 from the viewpoint that a stable visual field with a shield being fixed and without any distortion is obtained.

<<Active Energy Ray Curable Resin Composition>>

The active energy ray curable resin composition includes at least the following composition of a (meth)acrylate-based polymerizable compound, and may further include a photopolymerization initiator, and also components such as a filler and various functional additives, if necessary.

The composition of a (meth)acrylate-based polymerizable compound includes at least any of the following (A) and (B), and the following (C) and (D);
  (A) an ester (meth)acrylate of a trihydric alcohol having a main chain and a side chain each including an alkyl chain;
  (B) an ester di(meth)acrylate of ethylene oxide-modified bisphenol A;
  (C) a polyalkylene glycol di(meth)acrylate; and
  (D) an ester di(meth)acrylate of a dihydric alcohol having a main chain including a linear alkyl chain.

The ester (meth)acrylate here refers to (meth)acrylate having, in its molecule, an ester bond obtained by a reaction of an acid group (including an acid anhydride and an acid chloride) with a hydroxyl group, and having neither a urethane bond nor a siloxane bond.

The phrase "including at least any of the (A) and (B)" means all of an aspect of including the (A), an aspect of including the (B), and an aspect of including both the (A) and (B).

The ester (meth)acrylate (A) of a trihydric alcohol having a main chain and a side chain each including an alkyl chain includes a reaction product of a trihydric alcohol having a main chain and a side chain each including an alkyl chain and having hydroxyl groups, such as glycerin, trimethylolethane or trimethylolpropane with (meth)acrylic acid, and, in particular, trimethylolpropane triacrylate or the like is preferable.

The ester di(meth)acrylate (B) of ethylene oxide-modified bisphenol A includes one where n=4, 10 or 17 when the total number of ethylene oxide (EO) chain repeating units in its structure is defined as n, and, in particular, one where the total number n of ethylene oxide chain repeating units in its structure is 4 is preferable.

Examples of the polyalkylene glycol di(meth)acrylate (C) include polyethylene glycol diacrylate, polypropylene glycol diacrylate and tetramethylene glycol diacrylate, and, in particular, polyethylene glycol diacrylate or the like is preferable.

The polyalkylene glycol di(meth)acrylate (C) more preferably contains polyethylene glycol diacrylate having more than 8 ethylene oxide (EO) chain repeating units.

Examples of the ester di(meth)acrylate (D) of a dihydric alcohol having a main chain including a linear alkyl chain include 1,4-butanediol diacrylate, 1,6-hexanediol diacrylate, 1,9-nonanediol diacrylate and 1,10-decanediol diacrylate, and, in particular, 1,6-hexanediol diacrylate or the like is preferable.

The content of the trimethylolpropane triacrylate in the composition of a (meth)acrylate-based polymerizable compound is more preferably less than 24.8% by mass.

In addition, the content of the polyethylene glycol diacrylate in the composition of a (meth)acrylate-based polymerizable compound is more preferably less than 37.2% by mass.

—Photopolymerization Initiator—

Examples of the photopolymerization initiator include a photoradical polymerization initiator, a photo-acid generator, a bisazide compound, hexamethoxymethylmelamine and tetramethoxyglycoluril.

The photoradical polymerization initiator is not particularly limited and can be appropriately selected for any purpose, and examples thereof include (2,4,6-trimethylbenzoyl)-diphenyl-phosphine oxide, ethoxyphenyl (2,4,6-trimethylbenzoyl)phosphine oxide, bis(2,6-dimethylbenzoyl)-2,4,4-trimethylpentylphosphine oxide, bis(2,4,6-trimethylbenzoyl)-2,4,4-trimethylpentylphosphine oxide, bis(2,6-dichlorobenzoyl)-2,4,4-trimethylpentylphosphine oxide, 1-phenyl 2-hydroxy-2-methylpropan-1-one, 1-hydroxycyclohexyl phenyl ketone, 1-(4-isopropylphenyl)-2-hydroxy-2-methylpropan-1-one, 1,2-diphenylethanedione and methylphenylglyoxylate.

The content of the photopolymerization initiator in the active energy ray curable resin composition is not particularly limited, can be appropriately selected for any purpose, and is preferably 0.1% by mass to 10% by mass, more preferably 0.5% by mass to 8% by mass.

—Filler—

The filler is not particularly limited and can be appropriately selected for any purpose, and for example, any of an inorganic fine particle and an organic fine particle can be used. Examples of the inorganic fine particle include metal oxide fine particles of $SiO_2$, $TiO_2$, $ZrO_2$, $SnO_2$, $Al_2O_3$, and the like.

—Functional Additive—

Examples of the functional additive can include a leveling agent, a surface conditioner and a defoamer.

The active energy ray curable resin composition is cured by irradiation with an active energy ray. The active energy ray is not particularly limited and can be appropriately selected for any purpose, and examples thereof include electron beam, ultraviolet light, infrared light, laser light beam, visible light beam, ionizing radiations (X-ray, α-ray, β-ray, γ-ray and the like), microwave and high-frequency wave.

<<Properties of Structure Layer>>

The water contact angle on the surface of the structure layer is 26° or more and 74° or less; and the storage elastic modulus at 180° C. of the structure layer is less than 0.5 GPa.

In particular, when the composition of a (meth)acrylate-based polymerizable compound contains both components of the ester (meth)acrylate (A) of a trihydric alcohol having a main chain and a side chain each including an alkyl chain and the ester di(meth)acrylate (B) of ethylene oxide-modified bisphenol A, the effects of the present invention are sufficiently exerted in the water contact angle range of 26° or more and 74° or less.

When the composition of a (meth)acrylate-based polymerizable compound contains any component of the ester (meth)acrylate (A) of a trihydric alcohol having a main chain and a side chain each including an alkyl chain or the ester di(meth)acrylate (B) of ethylene oxide-modified bisphenol A, the water contact angle is more preferably in the range of 26° or more and 60° or less.

The water contact angle, the storage elastic modulus and the surface elastic modulus can be measured as follows.

[Water Contact Angle (°)]

The water contact angle is measured using a CA-V model manufactured by Kyowa Interface Science Co., Ltd. After 1 μL of water is dropped onto a sample surface, the contact angle after 11 seconds is measured. The contact angle is measured three times with the position of dropping of water onto the sample being changed, and the average value is determined.

[Storage Elastic Modulus (GPa, 180° C.)]

The active energy ray curable resin composition is placed on a PET film having a thickness of 50 μm subjected to a release treatment, sandwiched between the PET film and an additional PET film having a thickness of 50 μm subjected to a release treatment, made uniform with an applicator being slid from above the PET film, and cured by irradiation with UV light so that the amount of light accumulated is 1000 mJ/cm². After the curing, both the PET films subjected to a release treatment are peeled and the thickness of the cured product of the active energy ray curable resin composition is measured by a micrometer. The clearance of the applicator is adjusted so that the thickness of the active energy ray curable resin composition is about 100 μm, and the thickness of the final cured product is each measured and used for storage elastic modulus measurement. Measurement is made using RSA-3 manufactured by TA instruments Japan as the dynamic viscoelasticity measurement apparatus (DMA).

<Other Member(s)>

Examples of other member(s) above include an intermediate layer, a protection layer, a pressure-sensitive adhesion layer and an adhesion layer.

<<Intermediate Layer>>

An intermediate layer may also be provided between the transparent substrate and the structure layer depending on various objects.

For example, the intermediate layer can be provided to thereby enhance adhesiveness between the transparent substrate and the structure layer.

The refractive index of the intermediate layer is preferably close to the refractive index of the structure layer in order to prevent the variation in interference. Alternatively, the refractive index of the intermediate layer is preferably between the refractive index of the structure layer and the refractive index of the transparent substrate.

The intermediate layer may be formed by, for example, coating of the active energy ray curable resin composition. The active energy ray curable resin composition may be the same as or different from the constituent component of the structure layer. The coating method is not particularly limited and can be appropriately selected for any purpose, and examples thereof include wire bar coating, blade coating, spin coating, reverse roll coating, die coating, spray coating, roll coating, gravure coating, microgravure coating, lip coating, air knife coating, curtain coating and comma coating methods, and a dipping method.

The average thickness of the intermediate layer is not particularly limited, can be appropriately selected for any purpose, and is preferably 0.01 µm to 10 µm, more preferably 0.1 µm to 5 µm.

<<Protection Layer>>

The protection layer is not particularly limited as long as it prevents the structure layer from being damaged in production or molding processing of the transparent laminate in which the structure layer is formed, and can be appropriately selected for any purpose. The protection layer is peeled when the transparent laminate is used.

<<Pressure-Sensitive Adhesion Layer, Adhesion Layer>>

The pressure-sensitive adhesion layer and the adhesion layer are not particularly limited as long as these are formed on the transparent substrate and allow the transparent laminate to adhere to an object to be processed, an adherend and the like, and can be appropriately selected for any purpose.

The transparent laminate is particularly suitable for a film for in-mold molding, a film for insert molding, and a film for overlay molding.

The method for producing the transparent laminate is not particularly limited and can be appropriately selected for any purpose, and examples thereof include a method described below.

<Method for Producing Transparent Laminate>

Examples of the method for producing the transparent laminate include a method including an uncured resin layer formation step and a structure layer formation step, and such a method may further include other step, if necessary.

<<Uncured Resin Layer Formation Step>>

The uncured resin layer formation step is not particularly limited as long as it is a step of coating a transparent substrate with an active energy ray curable resin composition to form an uncured resin layer, and can be appropriately selected for any purpose.

The transparent substrate is as described in the section of the transparent laminate.

The active energy ray curable resin composition is as described in the section of the structure layer of the transparent laminate.

The uncured resin layer is formed by coating the transparent substrate with the active energy ray curable resin composition, and if necessary performing drying. The uncured resin layer may be a solid film or may be a film having fluidity due to a low molecular curable component contained in the active energy ray curable resin composition.

The coating method is not particularly limited and can be appropriately selected for any purpose, and examples thereof include wire bar coating, blade coating, spin coating, reverse roll coating, die coating, spray coating, roll coating, gravure coating, microgravure coating, lip coating, air knife coating, curtain coating and comma coating methods, and a dipping method.

The uncured resin layer is not cured because of being not irradiated with an active energy ray.

In the uncured resin layer formation step, the intermediate layer of the transparent substrate where the intermediate layer is formed may also be coated with the active energy ray curable resin composition to form the uncured resin layer.

The intermediate layer is as described in the section of the transparent laminate.

<<Structure Layer Formation Step>>

The structure layer formation step is not particularly limited as long as it is a step of closely attaching the uncured resin layer to a transfer master having any of fine protrusion and depression portions, and irradiating the uncured resin layer to which the transfer master is closely attached, with an active energy ray, to cure the uncured resin layer, thereby transferring any of the fine protrusion portions and depression portions to form a structure layer, and can be appropriately selected for any purpose.

—Transfer Master—

The transfer master has any of fine protrusion and depression portions.

The material, the size and the structure of the transfer master are not particularly limited, and can be appropriately selected for any purpose.

The method for forming any of fine protrusion and depression portions of the transfer master is not particularly limited and can be appropriately selected for any purpose, and such any of fine protrusion and depression portions is preferably formed by etching the surface of the transfer master with a photoresist having a predetermined pattern shape, as a protection film.

—Active Energy Ray—

The active energy ray is not particularly limited as long as it is an active energy ray that cures the uncured resin layer, can be appropriately selected for any purpose, and is, for example, as described in the section of the transparent laminate.

A specific example of the structure layer formation step is here described with reference to the drawings.

A transfer master where any of fine protrusion and depression portions is formed by etching the surface of the transfer master with a photoresist having a predetermined pattern shape, as a protection film, is used to form a structure layer.

[Configuration of Transfer Master]

Figure 3A:
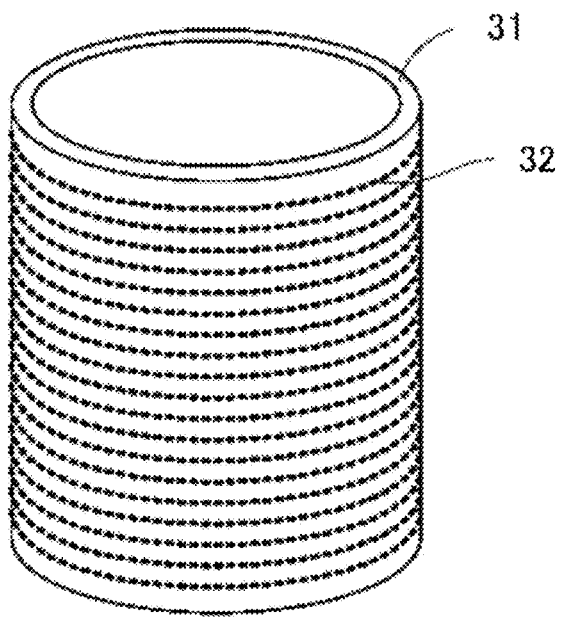
FIG. 3A is a perspective view illustrating one configuration example of a roll master being a transfer master.
Figure 3B:
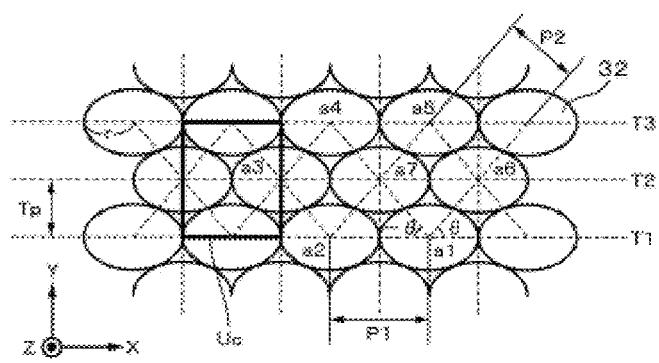
FIG. 3B is a plan view representing a part of the roll master illustrated in FIG. 3A, in an enlarged manner.
Figure 3C:
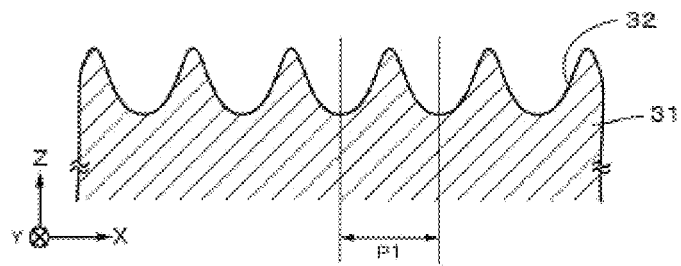
FIG. 3C is a cross-sectional view in a track T of FIG. 3B.

FIG. 3A is a perspective view illustrating one configuration example of a roll master being a transfer master. FIG. 3B is a plan view representing a part of the roll master illustrated in FIG. 3A, in an enlarged manner. FIG. 3C is a cross-sectional view in tracks T1, T3 . . . of FIG. 3B. A roll master 31 is a transfer master for production of a transparent laminate having the above configuration, more specifically, an master for molding of a plurality of protrusion portions or depression portions on the surface of the structure layer. The roll master 31 has, for example, a columnar or cylindrical shape, and the columnar surface or cylindrical surface serves as a molded surface for molding of a plurality of protrusion portions or depression portions on the surface of the structure layer. For example, a plurality of structures 32 are two-dimensionally arranged on the molded surface. In FIG. 3C, the structures 32 have a depression shape on the molded surface. As the material of the roll master 31, for example, glass can be used, but the material is not limited thereto.

The plurality of structures 32 arranged on the molded surface of the roll master 31 and the plurality of protrusion portions or depression portions arranged on the surface of the structure layer are in a reverse depression and protrusion relationship. That is, the arrangement, the size, the shape, the arrangement pitch, the height or depth, the aspect ratio and the like of the structures 32 of the roll master 31 are the same as those of the protrusion portions or depression portions of the structure layer.

[Roll Master Exposure Apparatus]

Figure 4:
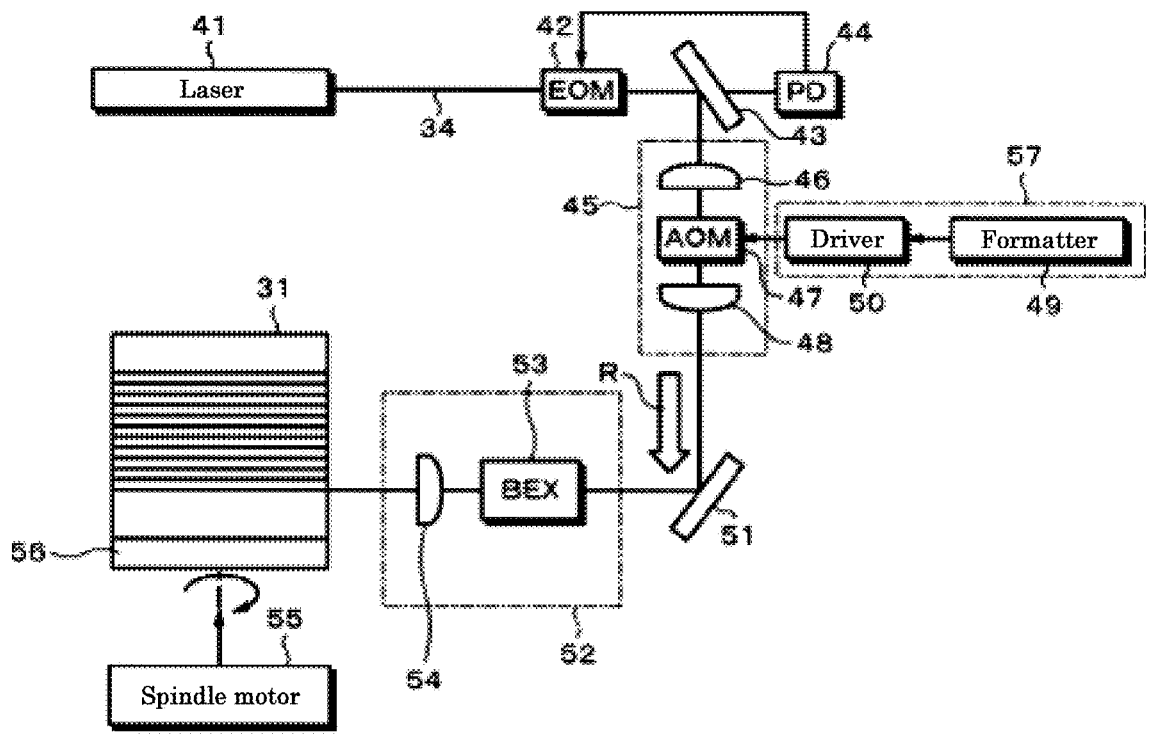
FIG. 4 is a schematic view illustrating one configuration example of a roll master exposure apparatus which produces a roll master.

FIG. 4 is a schematic view illustrating one configuration example of a roll master exposure apparatus for producing a roll master. The roll master exposure apparatus is configured based on an optical disk recording apparatus.

A laser light source 41 is a light source that exposes a resist attached in the form of a film onto the surface of the roll master 31 as a recording medium, and is, for example, one that emits laser light 34 for recoding at a wavelength λ of 266 nm. The laser light 34 emitted from the laser light source 41 goes straight as parallel beam, and enters an electro-optical element (EOM: Electro Optical Modulator) 42. The laser light 34 penetrating through the electro-optical element 42 is reflected in a mirror 43, and guided to a modulation optical system 45.

The mirror 43 is configured from a polarization beam splitter, and has a function of reflecting one polarization component and allowing other polarization component to penetrate through the mirror. The polarization component penetrating through the mirror 43 is received in a photo diode 44, and the electro-optical element 42 is controlled based on such a light reception signal for phase modulation of the laser light 34.

In the modulation optical system 45, the laser light 34 is collected by a collective lens 46 to an acousto-optic modulator (AOM) 47 made of glass ($SiO_2$) and the like. The laser light 34 is diffused due to intensity modulation by the acousto-optic modulator 47, and thereafter formed into parallel beam by a lens 48. The laser light 34 emitted from the modulation optical system 45 is reflected by a mirror 51, and horizontally and parallel guided onto a moving optical table 52.

The moving optical table 52 includes a beam expander 53 and an objective lens 54. The laser light 34 guided to the moving optical table 52 is formed into a desired beam shape by the beam expander 53, and thereafter a resist layer located on the roll master 31 is irradiated with such laser light 34 via the objective lens 54. The roll master 31 is mounted on a turntable 56 connected to a spindle motor 55. While the roll master 31 is then rotated and also the laser light 34 is moved in the height direction of the roll master 31, a resist layer formed on the peripheral side surface of the roll master 31 is intermittently irradiated with the laser light 34, thereby allowing a resist layer exposure step to be performed. A latent image formed has a substantially elliptical shape having a longitudinal axis in the circumferential direction. Movement of the laser light 34 is performed by movement of the moving optical table 52 in the direction of arrow R.

An exposure apparatus includes a control mechanism 57 that allows a latent image corresponding to a two-dimensional pattern of a hexagonal lattice or a quasi-hexagonal lattice illustrated in FIG. 2B and FIG. 3B to be formed into a resist layer. The control mechanism 57 includes a formatter 49 and a driver 50. The formatter 49 includes a polarity inversion portion, and the polarity inversion portion controls the timing of irradiation of the resist layer with the laser light 34. The driver 50 receives the output from the polarity inversion portion and controls the acousto-optic modulator 47.

In the roll master exposure apparatus, a polarity inversion formatter signal and a rotation controller are synchronized with respect to each track so that the two-dimensional pattern is spatially linked, thereby generating a signal, and the signal is subjected to intensity modulation by the acousto-optic modulator 47. Patterning can be made at a constant angular velocity (CAV) and at an appropriate number of rotations, an appropriate modulating frequency and an appropriate feed pitch to thereby record a hexagonal lattice or quasi-hexagonal lattice pattern.

[Resist Film Formation Step]

Figure 5A:
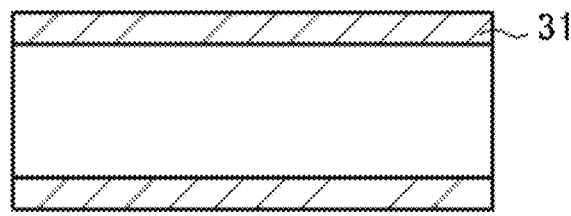
FIG. 5A is a process drawing for describing one example of a process for producing a roll master.
Figure 5B:
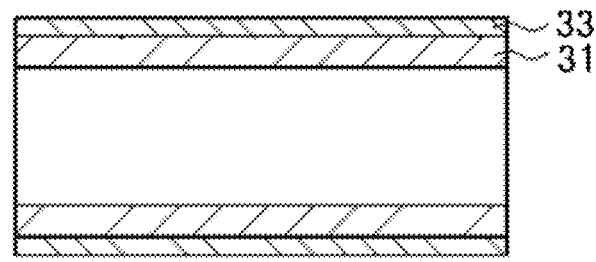
FIG. 5B is a process drawing for describing one example of a process for producing a roll master.

First, a columnar or cylindrical roll master 31 is prepared as illustrated in the cross-sectional view of FIG. 5A. The roll master 31 is, for example, a glass master. Next, a resist layer (for example, photoresist) 33 is formed on the surface of the roll master 31 as illustrated in the cross-sectional view of FIG. 5B. Examples of the material of the resist layer 33 include an organic resist and an inorganic resist. Examples of the organic resist include a novolac type resist and a chemically amplified type resist. Examples of the inorganic resist include a metal compound.

[Exposure Step]

Figure 5C:
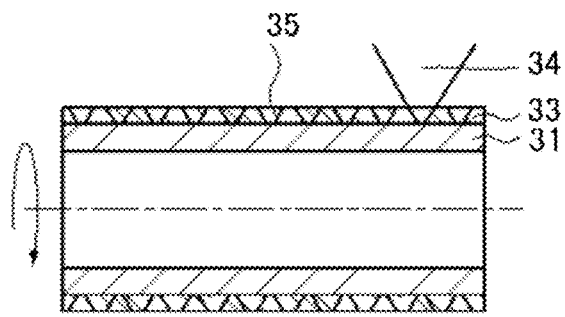
FIG. 5C is a process drawing for describing one example of a process for producing a roll master.

Next, as illustrated in the cross-sectional view of FIG. 5C, the resist layer 33 formed on the surface of the roll master 31 is irradiated with laser light (exposing beam) 34. Specifically, the roll master 31 is mounted on the turntable 56 of the roll master exposure apparatus illustrated in FIG. 4, and the roll master 31 is rotated and also the resist layer 33 is irradiated with the laser light (exposing beam) 34. Here, while the laser light 34 is moved in the height direction of the roll master 31 (direction parallel with the center axis of the columnar or cylindrical roll master 31), the resist layer 33 is intermittently irradiated with the laser light 34 and the entire surface thereof is thus exposed. Thus, a latent image 35 according to the trajectory of the laser light 34 is formed on the entire surface of the resist layer 33 at, for example, a pitch comparable with a wavelength of visible light.

The latent image 35 is, for example, arranged so as to form a plurality of rows of tracks T on the surface of the roll master, and also forms a hexagonal lattice pattern or a quasi-hexagonal lattice pattern. The latent image 35 has, for example, an elliptical shape whose longitudinal direction corresponds to the track extending direction.

[Development Step]

Figure 5D:
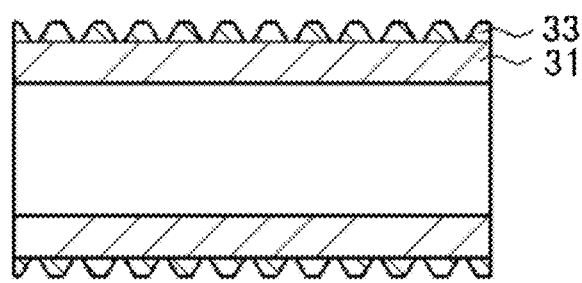
FIG. 5D is a process drawing for describing one example of a process for producing a roll master.

Next, for example, while the roll master 31 is rotated, a developer is dropped onto the resist layer 33 and the resist layer 33 is subjected to a development treatment. Thus, as illustrated in the cross-sectional view of FIG. 5D, a plurality of openings are formed in the resist layer 33. When the resist layer 33 is formed by a positive type resist, an area exposed to the laser light 34 is increased in terms of the dissolution speed in the developer as compared with an area not exposed, and therefore, a pattern corresponding to a latent image (exposed area) 35 is formed on the resist layer 33 as illustrated in the cross-sectional view of FIG. 5D. The pattern of openings is a predetermined lattice pattern such as a hexagonal lattice pattern or a quasi-hexagonal lattice pattern.

[Etching Step]

Figure 5E:
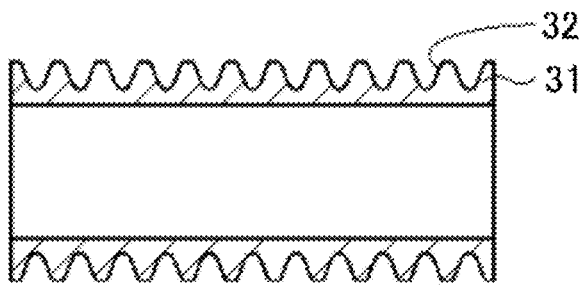
FIG. 5E is a process drawing for describing one example of a process for producing a roll master.

Next, the pattern (resist pattern) of the resist layer 33 formed on the roll master 31 is used as a mask to subject the surface of the roll master 31 to an etching treatment. Thus, a structure (depression portion) 32 having a cone shape can be obtained as illustrated in the cross-sectional view of FIG. 5E. The cone shape is preferably, for example, an elliptical cone shape or an elliptical frustum shape whose longitudinal direction corresponds to the track T extending direction. As the etching, for example, dry etching or wet etching can be used. An etching treatment and an ashing treatment can be here alternately performed to thereby form a pattern of cone-shaped structures 32. As described above, an intended roll master 31 is obtained.

[Transfer Treatment]

Figure 6A:
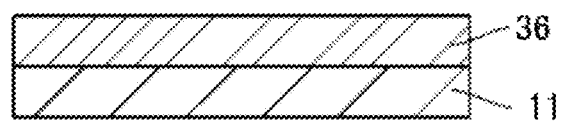
FIG. 6A is a process drawing for describing one example of a process for transferring fine protrusion portions or depression portions by a roll master.

A transparent substrate 11 where an uncured resin layer 36 is formed as illustrated in the cross-sectional view of FIG. 6A is prepared.

Figure 6B:
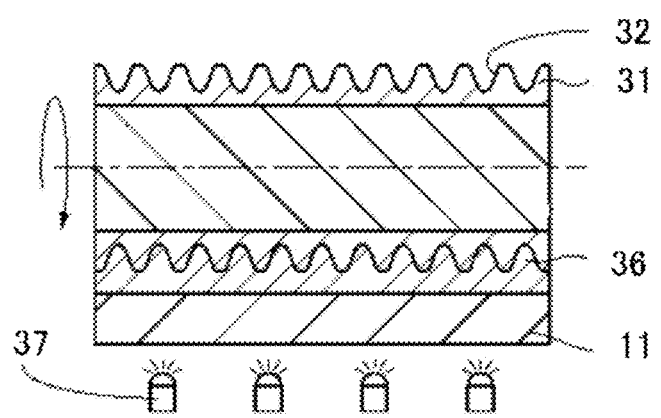
FIG. 6B is a process drawing for describing one example of a process for transferring fine protrusion portions or depression portions by a roll master.
Figure 6C:
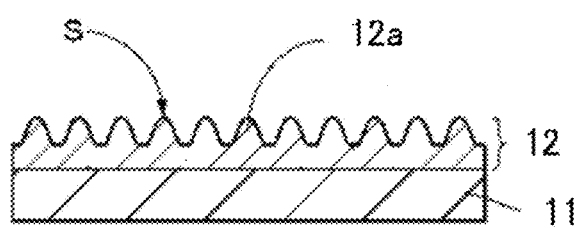
FIG. 6C is a process drawing for describing one example of a process for transferring fine protrusion portions or depression portions by a roll master.

Next, as illustrated in the cross-sectional view of FIG. 6B, the roll master 31 and the uncured resin layer 36 formed on the transparent substrate 11 are closely attached, and the uncured resin layer 36 is irradiated with an active energy ray 37 to cure the uncured resin layer 36, transferring any of fine protrusion and depression portions. A structure layer 12 where any of fine protrusion and depression portions 12a is formed and the transparent substrate 11 integrated therewith are peeled to thereby provide the transparent laminate 1 of the present invention (FIG. 6C).

When the transparent laminate is one including the structure layer on both surfaces of the transparent substrate as illustrated in FIG. 1B, it is obtained through the further following step.

Figure 7A:
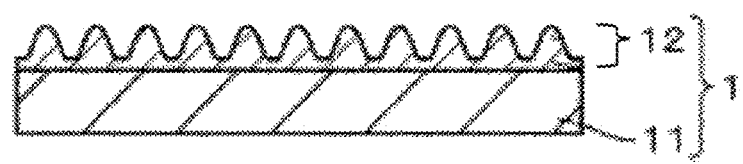
FIG. 7A is a process drawing for describing another example of a process for transferring fine protrusion portions or depression portions by a roll master.
Figure 7B:
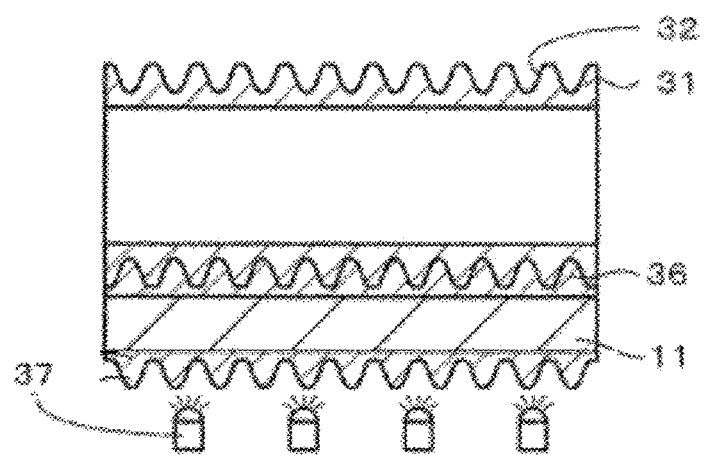
FIG. 7B is a process drawing for describing another example of a process for transferring fine protrusion portions or depression portions by a roll master.
Figure 7C:
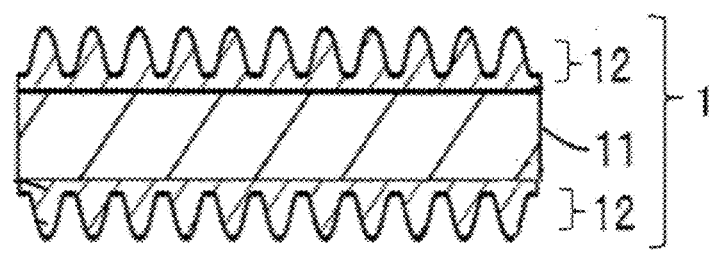
FIG. 7C is a process drawing for describing another example of a process for transferring fine protrusion portions or depression portions by a roll master.

The transparent laminate 1 obtained as above, where the structure layer is formed on one surface, is used (FIG. 7A), furthermore the roll master 31, and the uncured resin layer 36, with which an opposite surface of the transparent substrate 11 where the structure layer is formed on one surface is coated, are closely attached, thereafter the uncured resin layer 36 is cured by irradiation of the uncured resin layer 36 with an energy ray from an energy ray source 37, such as ultraviolet light, and the transparent substrate 11 integrated with the structure layer 12 cured is peeled, as illustrated in FIG. 7B. Thus, as illustrated in FIG. 7C, a transparent laminate 1 which includes the structure layer 12 having a plurality of structures 12a, on both surfaces of the transparent substrate 11, is obtained.

<<Other Method for Producing Transparent Laminate>>

The transparent laminate can also be produced using the roll master, obtained as above, by the following method.

A predetermined amount of the active energy ray curable resin composition is dropped on the roll master produced as above, covered with the transparent substrate, and extended by a roller over the roll master, thereafter irradiation with an energy ray such as ultraviolet light is performed through the transparent substrate to cure the active energy ray curable resin composition as a transfer material, and thereafter the transparent substrate integrated with the structure layer made by curing of the transfer material is released from the roll master. Thus, the transparent laminate of the present invention is obtained.

<Variants of Transparent Laminate>

<<First Variant>>

Figure 10A:
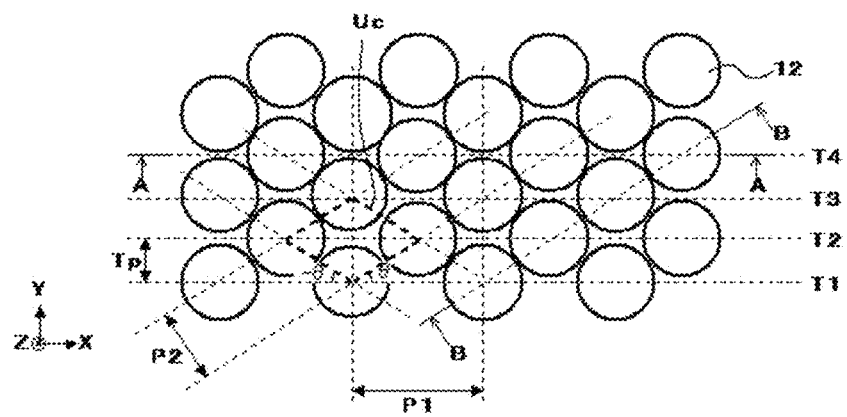
FIG. 10A is a plan view illustrating one example of a first variant of the transparent laminate of the present invention.
Figure 10B:
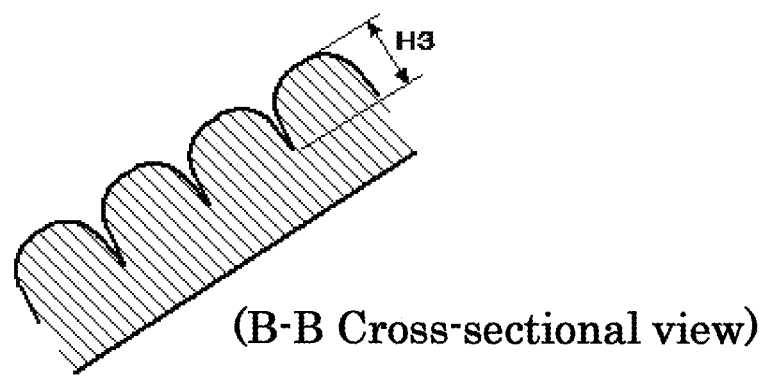
FIG. 10B is a cross-sectional view of FIG. 10A.
Figure 10C:
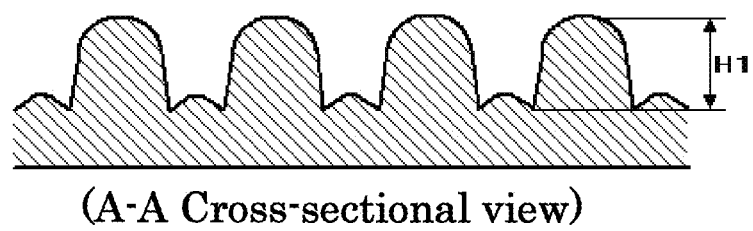
FIG. 10C is a cross-sectional view of FIG. 10A.

As illustrated in FIG. 10A, a plurality of structures 12a provided on the front surface of the transparent laminate 1 may be configured so as to form a tetragonal lattice pattern or quasi-tetragonal lattice pattern between adjacent tracks T. Similarly, a plurality of structures 12a provided on the rear surface of the transparent laminate 1 may be configured so as to form a tetragonal lattice pattern or quasi-tetragonal lattice pattern among three adjacent rows of tracks T.

The tetragonal lattice here refers to a square-shaped lattice. The quasi-tetragonal lattice refers to a distorted square-shaped lattice, unlike a square-shaped lattice. For example, when the structures 12a are linearly arranged, the quasi-tetragonal lattice refers to a tetragonal lattice where a square-shaped lattice is distorted in an arcuate manner, or refers to a tetragonal lattice where a square-shaped lattice is stretched in the arrangement direction (track direction) and distorted in an arcuate manner. When the structures 12a are arranged in a serpentine manner, the quasi-tetragonal lattice refers to a tetragonal lattice where a square-shaped lattice is distorted by serpentine arrangement of structures 12, or refers to a tetragonal lattice where a square-shaped lattice is stretched and distorted in the arrangement direction (track direction) and distorted by serpentine arrangement of structures 12.

When the structures 12a are arranged in a tetragonal lattice pattern or a quasi-tetragonal lattice pattern, the arrangement pitch P1 of structures 12a in the same track is preferably longer than the arrangement pitch P2 of structures 12a between two adjacent tracks. In addition, when the arrangement pitch of the structures 12a in the same track is defined as P1 and the arrangement pitch of the structures 12a between two adjacent tracks is defined as P2, P1/P2 preferably satisfies a relationship of $1.4<P1/P2 \leq 1.5$. Such a numerical range can allow the filling rate of structures 12a having an elliptical cone or elliptical frustum shape to be enhanced, resulting in an enhancement in optical adjustment function. In addition, the height or depth of each structure 12a in a direction of 45 degrees or in a direction of about 45 degrees to the track is preferably lower than the height or depth of each structure 12a in the track extending direction.

The height H3 in the arrangement direction (0 direction) of each structure 12a inclined to the track extending direction is preferably lower than the height H1 of each structure 12a in the track extending direction. That is, the heights H1 and H3 of such structures 12a preferably satisfy a relationship of $H1>H3$.

<<Second Variant>>

Figure 11:
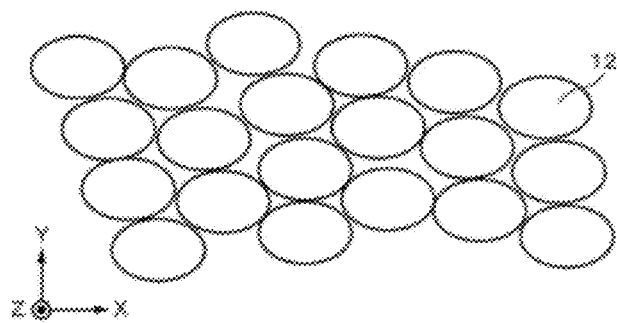
FIG. 11 is a plan view illustrating one example of a second variant of the transparent laminate of the present invention.

As illustrated in FIG. 11, a plurality of structures 12a may be two-dimensionally arranged on the surface of the transparent laminate 1 in a random (irregular) manner. At least one of the shape, the size and the height of each structure 12a may be randomly changed.

The method for producing an master for production of the transparent laminate 1 including the structures 12a, while, for example, a method where the surface of a metal substrate such as an aluminum substrate is anodized can be used therefor, is not particularly limited thereto.

In the second variant, a plurality of structures 12a can be two-dimensionally arranged in a random manner to thereby suppress the occurrence of variation in appearance.

<<Third Variant>>

Figure 12A:
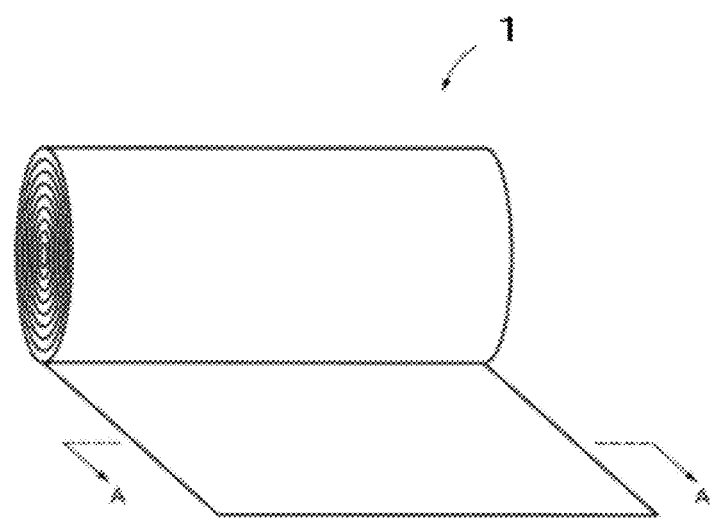
FIG. 12A is an outline view illustrating one example of a third variant of the transparent laminate of the present invention.

As illustrated in FIG. 12A, the transparent laminate 1 may have a band shape as a whole. Such a shape can allow the transparent laminate 1 to be more easily produced by a roll-to-roll step. In addition, the transparent laminate 1 can be wound in the form of a roll or the like to form a raw roll and thus easily handled.

Figure 12B:
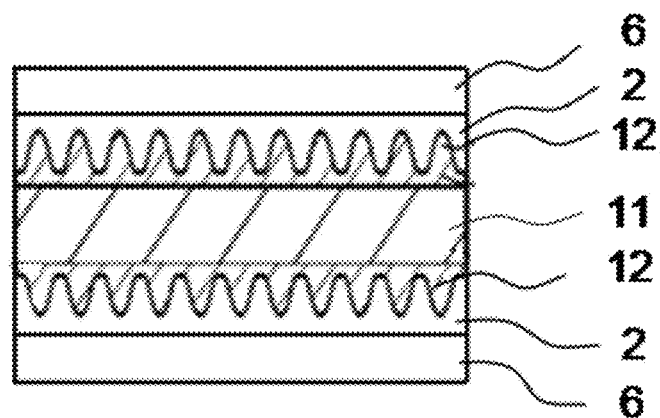
FIG. 12B is a cross-sectional view (B) along the A-A line of FIG. 12A.

When the above configuration is adopted as the configuration of the transparent laminate 1, a protection layer 6 that protects structures 12a can also be further provided on the outermost surface of the transparent laminate 1 with a pressure-sensitive adhesion layer 2 interposed therebetween, as illustrated in FIG. 12B. The reason is because, even when the transparent laminate 1 is wound in the form of a roll to form a raw roll, the structures 12a can be inhibited from being damaged to suppress deterioration in optical adjustment function. Herein, the protection layer 6 and the pressure-sensitive adhesion layer 2 are removed in use of the transparent laminate 1.

<Application Examples of the Transparent Laminate of the Present Invention>

The transparent laminate of the present invention exhibits good results with respect to all the items such as antireflection properties, permeation properties, antifouling properties, antifogging properties and protection properties in a well-balanced manner, and therefore can be applied, while utilizing such advantages, to a face protection mask, a display film, a display surface film for use in a display of a switchboard, a distribution board or the like (such a film can be suitable used as a film for use inside because of being particularly excellent in antifogging properties), a display surface film for use in a display surface of display equipment of a bike (such a film can be suitable used as a film for use inside because of being particularly excellent in antifogging properties), and a goggle for sports for use in horse racing and the like.

In particular, the transparent laminate is preferably used as a face protective optical element for medical use.

<<Face Protective Optical Element>>

The transparent laminate of the present invention, while utilizing advantages such as antireflection properties, permeation properties, antifouling properties, antifogging properties and protection properties, can be preferably used as a face protective optical element for medical use which protects the face from a flying object and simultaneously ensures a required visual field.

A medical face protection mask using the face protective optical element of the present invention is excellent in antifouling properties and abrasion resistance and furthermore instantly smooths the moisture included in the expired breath to prevent fogging, and therefore effectively prevents the occurrence of fogging and is excellent in permeation properties.

(Article)

An article can be formed by using the transparent laminate of the present invention and, if necessary, further using other member.

The article is not particularly limited and can be appropriately selected for any purpose, and examples thereof include a face protection mask, a display film, a display of a switchboard, a distribution board or the like, a display of display equipment of a bike, and a goggle for sports, described above.

In particular, as described above, the transparent laminate of the present invention can be used as a face protective optical element, and can be preferably applied to an article such as a medical face protection mask for use in a surgery, a dental therapy or the like. The face protective optical element of the present invention can be detachably mounted to a goggle type or face mask type optical element-mounting tool or can be fixed to a face mask to thereby provide a face protection tool.

Figure 8A:
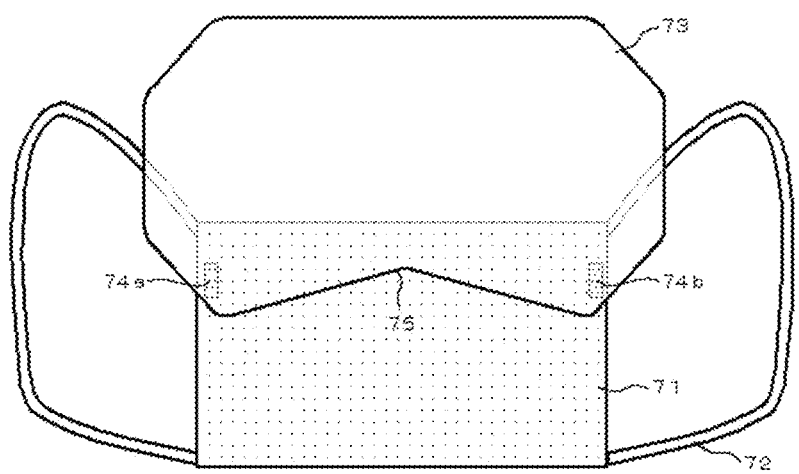
FIG. 8A is a plan view of a face protection mask of one embodiment of the present invention.
Figure 8B:
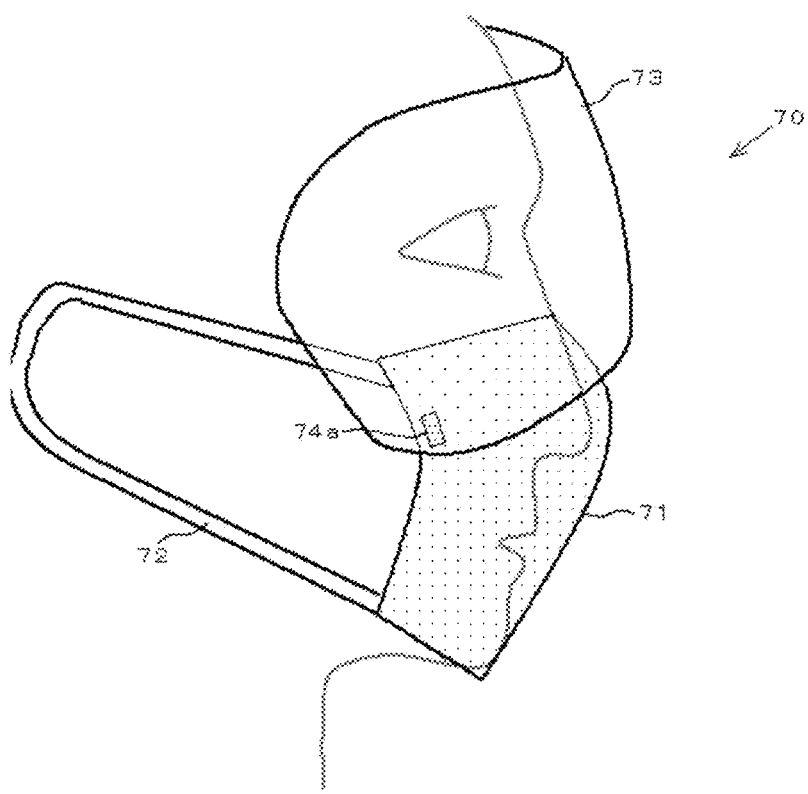
FIG. 8B is a perspective view of the face protection mask of one embodiment of the present invention, worn on the face.

FIG. 8A is a plan view of one embodiment of a face protection tool 70 where an optical element 1 for face protection of the present invention is fixed as an eye shield 73 to a face mask 71, and FIG. 8B is a perspective view of the face protection tool 70 worn on the face.

The face mask 71 partially covers the nose, mouth and jaw of a wearer, and is retained on the face by string 72 or the like. As the face mask 71, any medical face mask can be used, and, for example, one having aeration properties and having a multi-layer structure that prevents bacteria from invading can be used.

On the other hand, the optical element 1 for face protection is fixed as an eye shield 73 to the face mask 71 in junction regions 74a and 74b, the eye shield preventing any liquid or flying object from coming into the eyes of the wearer without obstructing the visual field of the wearer.

The eye shield 73 has a sufficiently large width as compared with the width of the face mask 71, and has a size that allows the circumference of the eyes of the wearer to be widely covered. In addition, the eye shield 73 has a depression 75 at the center of the lower side. When the face protection tool 70 is worn on the face, the depression 75 is present to thereby bend the eye shield 73 on the circumference of the nose of the wearer, allowing the eye shield 73 to have a curved surface along the face.

The junction regions 74a and 74b are provided on portions corresponding to both right and left ends of the face mask 71 and facing the lateral portions of the nose in wearing. The method for fixing the eye shield 73 and the face mask 71 in the junction regions 74a and 74b can include ultrasonic welding, heat bonding, and mechanical jointing by a rivet and the like. The size of each of the junction regions 74a and 74b may be any size as long as the eye shield 73 can be secured, and can have, for example, a width of 3 mm to 15 mm and a length of 5 mm to 30 mm. Thus, the eye shield 73 is not required to be pushed to the face by the string 72, and the face protection tool 70 can be simply detached.

In the present invention, the optical element 1 for face protection of the present invention, for use as the eye shield 73, may be detachably mounted to the face mask 71.

The optical element 1 for face protection for use as the eye shield as described above is obtained as the transparent laminate by the above production method, thereafter cut to a predetermined size for mounting to the face protection tool, and thus used. In production and processing of the article such as the face protection tool, including such a cutting step, the surface protection film may be disposed on the transparent laminate surface in order to protect the transparent laminate surface.

An article including the transparent laminate of the present invention can be formed by in-mold molding, insert molding or overlay molding.

The transparent laminate may be formed on a part or the entire surface of the article.

The method for producing the article is not particularly limited, can be appropriately selected for any purpose, and examples preferably include the following production method by in-mold molding.

<<Method for Producing Article Including the Transparent Laminate of the Present Invention>>

Examples of the method for producing the article include a production method including a heating step, a transparent laminate molding step and an injection molding step, and such a method may further include other step, if necessary.

<<Heating Step>>

The heating step is not particularly limited as long as it is a step of heating the transparent laminate, and can be appropriately selected for any purpose.

The transparent laminate is the transparent laminate of the present invention.

The heating is not particularly limited, can be appropriately selected for any purpose, and is preferably infrared light heating.

The heating temperature is not particularly limited and can be appropriately selected for any purpose, and when the transparent substrate is a resin substrate, the heating temperature is preferably around the glass transition temperature of the resin substrate, or equal to or higher than the glass transition temperature thereof.

The heating time is not particularly limited, and can be appropriately selected for any purpose.

<<Transparent Laminate Molding Step>>

The transparent laminate molding step is not particularly limited as long as it is a step of molding the transparent laminate heated, into a desired shape, and can be appropriately selected for any purpose, and examples thereof include a step of closely attaching the transparent laminate to a predetermined mold, and molding it into a desired shape by air pressure.

<<Injection Molding Step>>

The injection molding step is not particularly limited as long as it is a step of injecting a molding material to the transparent substrate of the transparent laminate molded into a desired shape, to mold the molding material, and can be appropriately selected for any purpose.

Examples of the molding material include a resin. Examples of the resin include an olefin-based resin, a styrene-based resin, an ABS resin (acrylonitrile-butadiene-styrene copolymer), an AS resin (acrylonitrile-styrene copolymer), an acrylic resin, a urethane-based resin, an unsaturated polyester resin, an epoxy resin, a polyphenylene oxide-polystyrene-based resin, polycarbonate, polycarbonate-modified polyphenylene ether, polyethylene terephthalate, polysulfone, polyphenylene sulfide, polyphenylene oxide, polyetherimide, polyimide, liquid crystal polyester, a polyallyl-based heat resistant resin, various composite resins and various modified resins.

The method of the injection is not particularly limited and can be appropriately selected for any purpose, and examples thereof include a method where the molding material molten is poured to the transparent substrate of the transparent laminate closely attached to a predetermined mold.

The method for producing the article is preferably performed using an in-mold molding apparatus, an insert molding apparatus or an overlay molding apparatus.

One example of the method for producing the article including the transparent laminate of the present invention is here described with reference to the drawings. The production method is a production method using an in-mold molding apparatus.

First, a transparent laminate 500 is heated. The heating is preferably infrared light heating.

Figure 9A:
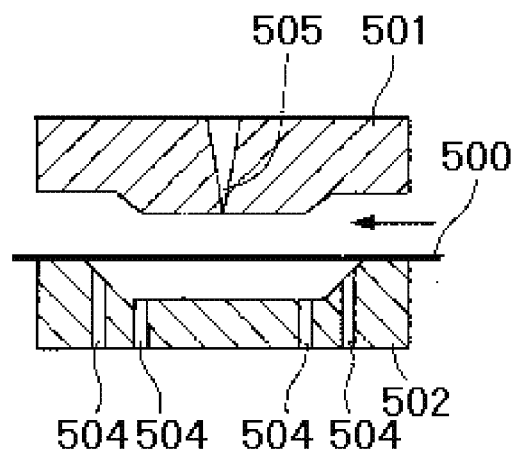
FIG. 9A is a process drawing for describing one example of production of the article of the present invention by in-mold molding.

Subsequently, the transparent laminate 500 heated is arranged at a predetermined position between a first mold 501 and a second mold 502, as illustrated in FIG. 9A. Such arrangement here is made so that the transparent substrate of the transparent laminate 500 faces the first mold 501 and the structure layer thereof faces the second mold 502. In FIG. 9A, the first mold 501 is secured and the second mold 502 is movable.

Figure 9B:
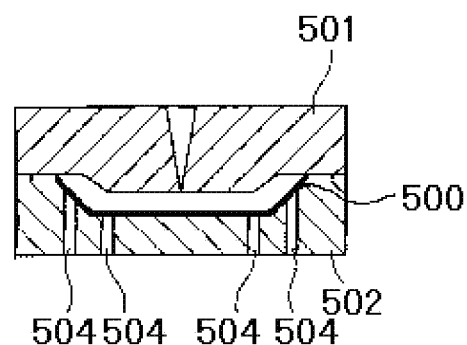
FIG. 9B is a process drawing for describing one example of production of the article of the present invention by in-mold molding.

After the transparent laminate 500 is arranged between the first mold 501 and the second mold 502, the first mold 501 and the second mold 502 are clamped. Subsequently, the transparent laminate 500 is suctioned through a suction hole 504 opened on the cavity surface of the second mold 502, and the transparent laminate 500 is attached to the cavity surface of the second mold 502. The cavity surface is thus given the shape by the transparent laminate 500. The outer circumference of the transparent laminate 500 may also be secured and positioned by a film pressing mechanism not illustrated. Thereafter, an unnecessary part of the transparent laminate 500 is trimmed away (FIG. 9B).

When the second mold 502 has no suction hole 504 and the first mold 501 has a compressed air hole (not illustrated), compressed air is fed through the compressed air hole of the first mold 501 to the transparent laminate 500, thereby allowing the transparent laminate 500 to be attached to the cavity surface of the second mold 502.

Figure 9C:
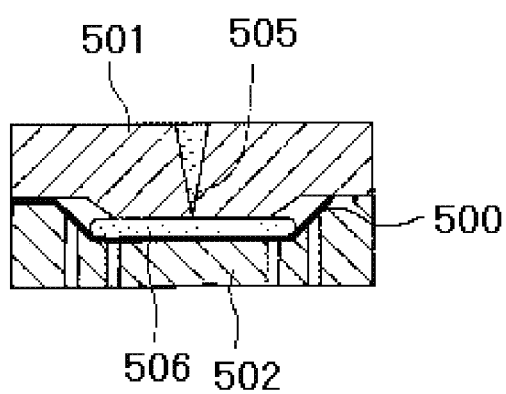
FIG. 9C is a process drawing for describing one example of production of the article of the present invention by in-mold molding.
Figure 9D:
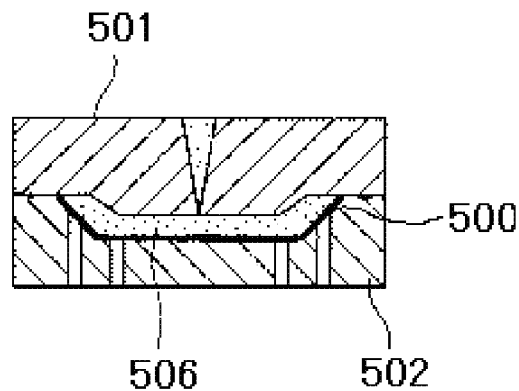
FIG. 9D is a process drawing for describing one example of production of the article of the present invention by in-mold molding.

Subsequently, the molding material 506 molten is injected through a gate 505 of the first mold 501 towards the transparent substrate of the transparent laminate 500, and poured into the cavity formed by clamping the first mold 501 and the second mold 502 (FIG. 9C). Thus, the molding material 506 molten is filled in the cavity (FIG. 9D). Furthermore, after completion of filling of the molding material 506 molten, the molding material 506 molten is cooled to a predetermined temperature and solidified.

Figure 9E:
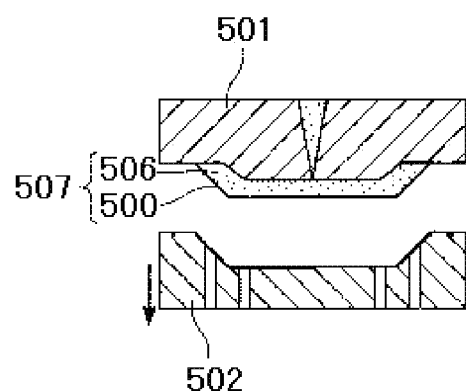
FIG. 9E is a process drawing for describing one example of production of the article of the present invention by in-mold molding.
Figure 9F:
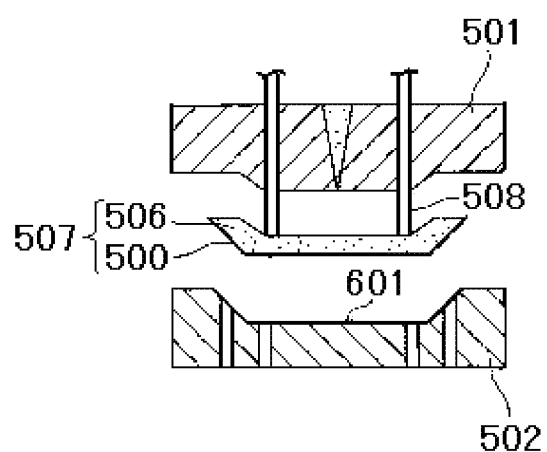
FIG. 9F is a process drawing for describing one example of production of the article of the present invention by in-mold molding.

Thereafter, the second mold 502 is moved to perform opening of the first mold 501 and the second mold 502 (FIG. 9E). Thus, an article 507 is obtained in which the transparent laminate 500 is formed on the surface of the molding material 506 and which is in-mold molded into a desired shape.

Finally, an ejection pin 508 is pushed out from the first mold 501 to take out the resulting article 507.

When the shape is more complicated, pre-forming may be performed in advance by the same steps as above without any additional resin of the molding material added, and thereafter actual molding may be performed to produce the article.

EXAMPLES

Hereinafter, the present invention is more specifically described with reference to Examples and Comparative Examples, but the present invention is not limited thereto.

In Examples below, respective measurements and evaluations were performed as follows.

<Water Contact Angle (°)>

The water contact angle was measured using a CA-V model manufactured by Kyowa Interface Science Co., Ltd. After 1 μL of water was dropped onto a sample surface, the contact angle after 11 seconds was measured. The contact angle was measured three times with the position of dropping of water onto the sample being changed, and the average value was determined.

<Storage Elastic Modulus (GPa, 180° C.)>

The active energy ray curable resin composition was placed on a PET film having a thickness of 50 μm subjected to a release treatment, sandwiched between the PET film and an additional PET film having a thickness of 50 μm subjected to a release treatment, made uniform with an applicator being slid from above the PET film, and cured by irradiation with UV light so that the amount of light accumulated was 1000 mJ/cm². After the curing, both the PET films subjected to a release treatment were peeled and the thickness of the cured product of the active energy ray curable resin composition was measured by a micrometer. The clearance of the applicator was adjusted so that the thickness of the active energy ray curable resin composition was about 100 μm, and the thickness of the final cured product was each measured and used for storage elastic modulus measurement. Measurement was made using RSA-3 manufactured by TA instruments Japan as the dynamic viscoelasticity measurement apparatus (DMA).

<Surface Elastic Modulus (GPa, Room Temperature)>

The elastic modulus of the surface of the transparent laminate was measured using PICODENTOR HM500 manufactured by Fisher instruments K.K. Japan.

<Mandrel Test (mm)>

The mandrel radius was sequentially changed using a PI-801 paint film bending tester manufactured by Tester Sangyo Co., Ltd. to measure the mandrel radius, where any crack occurred on the structure layer of the transparent laminate, according to JIS K5600-5-1. A smaller mandrel radius indicates better bending properties. In addition, the minimum mandrel radius is 2 mm, and therefore the description "2 mm>" represents no occurrence of any crack.

<Tensile Elongation at Break (%)>

The active energy ray curable resin composition was placed on a PET film having a thickness of 50 µm subjected to a release treatment, sandwiched between the PET film and an additional PET film having a thickness of 50 µm subjected to a release treatment, made uniform with an applicator, whose clearance was adjusted so that the thickness of the cured product layer was about 100 µm, being slid from above the PET film, and cured by irradiation with UV light so that the amount of light accumulated was 1000 mJ/cm². After the curing, both the PET films subjected to a release treatment were peeled and the thickness of the cured product of the active energy ray curable resin composition was measured by a micrometer.

The cured product layer was punched into a strip of 10 mm in width and 80 mm in length to provide a sample.

A tensile tester (Autograph AG-X 5 kN manufactured by Shimadzu Corporation) was used to secure both ends of the sample and pull them at a tensile rate of 300 mm/min, measuring the rate of elongation at break of the sample relative to the initial state.

<Punching Test (Whether any Crack Occurred or not During Cutting)>

A sample of the transparent laminate of the present invention was subjected to a punching test with a Thomson blade die having a thickness of 0.7 mm and a blade edge angle of 42° by use of a hand toggle press manufactured by Matex Seiko Co., Ltd., the cut surface after punching was observed by an optical microscope, and whether any crack occurred or not was confirmed. Whether any crack occurred or not and the size of such a crack were evaluated based on the following rating method.

Rating method: the distance L1 from the edge portion of the cross-section of the transparent laminate to the end of any crack in a 90-degree direction was measured. Such measurement was performed at 10 points where any crack occurred. The average value of L1 at 10 points was determined. The resulting value was defined as the crack length and evaluated according to the following criteria.

—Criteria—

Large crack: the crack length was 100 µm or more

Medium crack: the crack length was 50 µm or more and less than 100 µm

Small crack: the crack length was 5 µm or more and less than 50 µm

No crack: the crack length was less than 5 µm

<Protection Film Peeling Force (N/25 mm)>

The peeling force was measured by a 90-degree peeling test according to JIS Z-0237. A protection film having a commercially available acrylic pressure-sensitive adhesion layer cut to 25 mm in width was pasted to the structure layer on the transparent laminate, and left to stand for 24 hours. Thereafter, the protection film was peeled from the sample at a tensile rate of 300 mm/min to measure the peeling force in peeling, by use of a tensile compression testing machine SV-55C-2H manufactured by Imada-SS Corporation. The peeling force is preferably 0.1 N/25 mm to 0.8 N/25 mm in terms of handling.

<Fingerprint Resistance (Fingerprint Wiping-Off Properties)>

Fingerprints were put on the sample (the structure layer on the transparent laminate) and thereafter wiped with water by a wiping cloth, and the degree of wiping off the fingerprints was visually confirmed. The results after wiping with water once and after wiping with water five times were confirmed. As the wiping cloth, Savina Minimax (manufactured by KB Seiren Ltd.) being a wiping cloth for a clean room was used.

<Antifogging Properties>

The antifogging properties were evaluated by placing the sample of the transparent laminate of the present invention at a distance of about 2.5 cm from the mouth and breathing on the sample. The time for breathing was about 3 seconds. Such evaluation was performed continuously three times. As a result, a case where no fogging occurred was rated as "Good", and a case where fogging occurred was rated as "Poor".

Example 1

<Production of Transfer Master (Glass Roll Master) Having Fine Depression Portions>

First, a glass roll master having an outer diameter of 126 mm was prepared, and a resist layer was formed on the surface of the glass roll master as follows. That is, a photoresist was diluted with a thinner to a mass ratio of 1/10, and the columnar surface of the glass roll master was coated with the resist diluted, by a dipping method, so that the average thickness was about 70 nm, thereby forming a resist layer. Next, the glass roll master was conveyed to the roll master exposure apparatus illustrated in FIG. 4, and the resist layer was exposed to thereby allow a latent image being continuous in a helix and forming a hexagonal lattice pattern among three adjacent rows of tracks to be patterned on the resist layer. Specifically, a region where a hexagonal lattice exposure pattern was to be formed was irradiated with laser light at 0.50 mJ/m in an image shape, to form a hexagonal lattice exposure pattern.

Next, the resist layer on the glass roll master was subjected to a development treatment, and the resist layer on the area exposed was dissolved for development. Specifically, the glass roll master not subjected to development was mounted on the turntable of a developing machine not illustrated, and a developer was dropped on the surface of the glass roll master with the glass roll master being rotated together with the turntable, to develop the resist layer on the surface. Thus, a resist glass master where the resist layer was opened in the hexagonal lattice pattern was obtained.

Next, a roll etching apparatus was used to perform plasma etching in a $CHF_3$ gas atmosphere. Thus, etching was advanced in only an area of the hexagonal lattice pattern, exposed from the resist layer, on the surface of the glass roll master and no etching was advanced in other area due to the resist layer serving as a mask, to form depression portions having an elliptical cone shape on the glass roll master. Here, the amount (depth) of etching was adjusted by the etching time. Finally, the resist layer was completely removed by $O_2$ ashing, thereby providing a glass roll master having a depression-shaped hexagonal lattice pattern.

<Production of Transparent Laminate>

Next, the roll master obtained as above was used to produce a transparent laminate by UV imprinting. Specifically, such production was performed as follows.

First, an UV curing resin composition having the following composition (component table was shown in Table 1-1 below) was put several drops on the master having a moth-eye shape, produced as above, covered with a polycarbonate film (C000, manufactured by Sumitomo Chemical Co., Ltd.) as a transparent substrate, and extended by a roller over the master.

Thereafter, irradiation with ultraviolet light at 1000 mJ/cm² was performed through the polycarbonate film, to cure the resin, and thereafter releasing from the master was conducted to provide a transparent laminate.

—Ultraviolet Curable Resin Composition for Structure Layer—

Trimethylolpropane triacrylate
(miramer M300 (manufactured by Miwon Speciality Chemical Co., Ltd.))
24.27% by mass
Polyethylene glycol diacrylate
(NK ester A-600 (manufactured by Shin-Nakamura Chemical Co., Ltd.))
23.00% by mass
1,6-Hexanediol diacrylate
(miramer M200 (manufactured by Miwon Speciality Chemical Co., Ltd.))
45.73% by mass
2,4,6-Trimethylbenzoyl-diphenyl-phosphine oxide
(polymerization initiator: Lucilin TPO (manufactured by BASF S.E))
7.00% by mass
Herein, Miwon means Miwon specialty chemical Co., Ltd.

In the structure layer of the resulting transparent laminate, the average thickness was 3 μm, the average distance (Pm) of the protrusion portions was 178 nm, the average height (Hm) of the protrusion portions was 245 nm, and the average aspect ratio (Hm/Pm) was 1.38.

In order to evaluate properties of the resulting transparent laminate, respective items of water contact angle (°), storage elastic modulus (GPa, 180° C.), surface elastic modulus (GPa, room temperature), mandrel test (mm), tensile elongation at break (%), punching test, protection film peeling force (N/25 mm), fingerprint resistance and antifogging properties were measured and evaluated according to the above methods. The results are shown in Table 2-1.

Examples 2 to 6

Each transparent laminate was obtained in the same manner as in Example 1 except that the ultraviolet curable resin composition for the structure layer in Example 1 was changed to each composition shown in Table 1-1 below.

In order to evaluate properties of each transparent laminate obtained, the same measurements and evaluations as in Example 1 were performed. The results are shown in Table 2-1.

Comparative Examples 1 to 7

Each transparent laminate was obtained in the same manner as in Example 1 except that the ultraviolet curable resin composition for the structure layer in Example 1 was changed to each composition shown in Table 1-2 below.

In order to evaluate properties of each transparent laminate obtained, the same measurements and evaluations as in Example 1 were performed. The results were shown in Table 2-2. In Comparative Example 4, the result of antifogging properties was poor and antifogging performance demanded in the present invention was not achieved. Therefore, no measurement was performed with respect to the residual evaluation items in some cases, and in such cases, such information was shown in the Table.

TABLE 1-1

| | Component | Total number of ethylene oxide (EO) chain repeating units | Product name Manufacturer | Example 1 | Example 2 | Example 3 | Example 4 | Example 5 | Example 6 |
|---|---|---|---|---|---|---|---|---|---|
| (A) | Trimethylol propane triacrylate | 0 | miramer M300 Miwon | 24.27 | 20.00 | 24.27 | — | — | 23.58 |
| | Pentaerythrilol tetracrylate | 0 | Alonix M303 Toagosel Co., Ltd. | — | — | — | — | — | — |
| | Urethane acrylate | 0 | Shiko UV170OB Nippon Synthetic Chemical Industry Co., Ltd. | — | — | — | — | — | — |
| (D) | 1,6-Hexanediol diacrylate | 0 | miramer M100 Miwon | 45.73 | 50.00 | 38.03 | 29.40 | 29.40 | 44.42 |
| (B) | Ethylene oxide-modified bisphenol A diacrylate | n = 4 | miramer M240 Miwon | — | — | — | 33.30 | 33.30 | 8.50 |
| (C) | Polyethylene glycol diacrylate | n = 14 | NK ester A-600 Shin-Nakamura Chemical Co., Ltd. | 23.00 | 23.00 | 30.00 | — | 16.65 | 18.50 |
| | | n = 9 | NK ester A-400 Shin-Nakamura Chemical Co., Ltd. | — | — | — | 33.30 | — | — |
| | | n = 4 | Alonix M240 Toagosel Co., Ltd. | — | — | — | — | 16.65 | — |
| | Acrytoylmorpholine | 0 | ACHO KJ Chemicals Corporation | — | — | — | — | — | — |
| Polymerization Initiator | 2,4,6-Trimethylbenzoyl-diphenyl-phosphate oxide | | Luclin TPO BASF S.E | 7.00 | 7.00 | 7.60 | 4.00 | 4.00 | 5.00 |
| | Total | | | 100.00 | 100.00 | 100.00 | 100.00 | 100.00 | 100.00 |

Miwon . . . Miwon speciatly chemical Co., Ltd.

TABLE 1-2

|  | Component | Total number of ethylene oxide (EO) chain repeating units | Product name Manufacturer | Comp. Example 1 | Comp. Example 2 | Comp. Example 3 | Comp. Example 4 | Comp. Example 5 | Comp. Example 6 |
|---|---|---|---|---|---|---|---|---|---|
| (A) | Trimethylol propane triacrylate | 0 | miramer M300 Miwon | 24.27 | 24.27 | 30.00 | — | — | — |
|  | Pentaerythrilol tetracrylate | 0 | Alonix M303 Toagosel Co., Ltd. | — | — | — | — | 27.90 | 21.70 |
|  | Urethane acrylate | 0 | Shiko UV170OB Nippon Synthetic Chemical Industry Co., Ltd. | — | — | — | — | 20.34 | 15.82 |
| (D) | 1,6-Hexanediol diacrylate | 0 | miramer M200 Miwon | 32.73 | 32.04 | 40.00 | 29.40 | — | — |
| (B) | Ethylene oxide-modified bisphenol A diacrylate | n = 4 | miramer M240 Miwon | — | — | — | 33.30 | — | — |
| (C) | Polyethylene glycol diacrylate | n = 14 | NK ester A-600 Shin-Nakamura Chemical Co., Ltd. | 36.00 | 38.84 | 23.00 | — | — | — |
|  |  | n = 9 | NK ester A-400 Shin-Nakamura Chemical Co., Ltd. | — | — | — | — | — | — |
|  |  | n = 4 | Alonix M240 Toagosel Co., Ltd. | — | — | — | 33.30 | 10.00 | 30.00 |
|  | Acrytoylmorpholine | 0 | ACHO KJ Chemicals Corporation | — | — | — | — | 36.72 | 28.56 |
| Polymerization Initiator | 2,4,6-Trimethylbenzoyl-diphenyl-phosphate oxide |  | Luclin TPO BASF S.E | 7.00 | 4.85 | 7.00 | 4.00 | 5.04 | 3.82 |
|  |  |  | Total | 100.00 | 100.00 | 100.00 | 100.00 | 100.00 | 100.00 |

Miwon . . . Miwon speciatly chemical Co., Ltd.

TABLE 2-1

|  |  | Example 1 | Example 2 | Example 3 | Example 4 | Example 5 | Example 6 |
|---|---|---|---|---|---|---|---|
| Water contact angle (°) | | 57.0 | 58.1 | 30.3 | 28.7 | 29.9 | 74.0 |
| Storage elastic modulus (GPa, 180° C.) | | 0.38 | 0.40 | 0.34 | 0.13 | 0.10 | 0.35 |
| Surface elastic modulus (GPa, room temperature) | | 1214 | 1271 | 998 | 740 | 1110 | 1050 |
| Mandrel test (mm) | | 2 mm> | 2 mm> | 2 mm> | 2 mm> | 2 mm> | 2 mm> |
| Tensile elongation at break (%) | | 1.62 | 1.06 | 2.30 | 4.13 | 3.82 | 1.80 |
| Punching test (cutting test) | | No crack | No crack | No crack | No crack | No crack | No crack |
| Protection film, peeling force (N/25 mm) | | 0.18 | 0.12 | 0.37 | 0.50 | 0.46 | 0.11 |
| Fingerprint resistance (fingerprint wiping-off properties) | Wiping with water once | Completely wiped off | Completely wiped off | Slightly remained | Slightly remained | Slightly remained | Completely wiped off |
| | Wiping with water five times | Completely wiped off | Completely wiped off | Completely wiped off | Completely wiped off | Completely wiped off | Completely wiped off |
| Antifogging properties | | Good | Good | Good | Good | Good | Good |

TABLE 2-2

|  | Comparative Example 1 | Comparative Example 2 | Comparative Example 3 | Comparative Example 4 | Comparative Example 5 | Comparative Example 6 |
|---|---|---|---|---|---|---|
| Water contact angle (°) | 24.1 | 19.0 | 60.0 | 75.2 | 48.9 | 12.1 |
| Storage elastic modulus (GPa, 180° C.) | 0.31 | 0.26 | 0.50 | Not measured | 0.93 | 0.63 |
| Surface elastic modulus (GPa, room temperature) | 850 | 780 | 1380 | Not measured | 5360 | 3240 |
| Mandrel test (mm) | 2 mm> | 2 mm> | 2 mm> | Not measured | 6 mm | 2 mm> |
| Tensile elongation at break (%) | 2.50 | 2.77 | 0.60 | Not measured | 0.40 | 0.62 |
| Punching test (cutting test) | No crack | No crack | Small crack | Not measured | Large crack | Medium crack |
| Protection film, peeling force (N/25 mm) | 0.85 | 0.95 | 0.11 | Not measured | 0.15 | 0.93 |
| Fingerprint resistance (fingerprint wiping-off properties) Wiping with water once | Hardly wiped off | Hardly wiped off | Completely wiped off | Completely wiped off | Completely wiped off | Hardly wiped off |
| Fingerprint resistance (fingerprint wiping-off properties) Wiping with water five times | Hardly wiped off | Hardly wiped off | Completely wiped off | Completely wiped off | Completely wiped off | Hardly wiped off |
| Antifogging properties | Good | Good | Good | Poor | Good | Good |

It can be confirmed from the above experimental results that the transparent laminate of the present invention is a transparent laminate which bears proper close attachment properties to the surface protection film, which can effectively prevent an adverse effect: breakage of fine depression and protrusion shapes generated; due to too good close attachment properties to the surface protection film and which is excellent in antifouling properties, antifogging properties and the like, and furthermore is a transparent laminate excellent in crack resistance because the structure layer thereof has proper hardness and flexibility.

INDUSTRIAL APPLICABILITY

The transparent laminate of the present invention can be used as an antireflection film, a protection sheet or the like. The transparent laminate of the present invention can be applied to a display film, a display surface film for use in a display of a switchboard, a distribution board or the like, a display surface film for use in a display surface of display equipment of a bike, a goggle for sports, and the like, and can be preferably applied particularly to a medical face protection mask for use in a surgery, a dental therapy or the like.

REFERENCE SINGS LIST 1 transparent laminate
6 protection layer
11 transparent substrate
12 structure layer
12a structure
14 projection
15 curved surface portion
31 roll master
32 structure
33 resist layer
34 laser light
35 latent image
36 uncured resin layer
37 active energy ray
41 laser light source
42 electro-optical element
43 mirror
44 photo diode
45 modulation optical system
46 collective lens
47 acousto-optic modulator
48 lens
49 formatter
50 driver
51 mirror
52 moving optical table
53 beam expander
54 objective lens
55 spindle motor
56 turntable
57 control mechanism
70 face protection tool
71 face mask
72 string
73 eye shield
74a, 74b junction regions
75 depression

The invention claimed is:

1. A transparent laminate comprising:
a transparent substrate; and
a structure layer,
wherein the structure layer contains protrusion portions, depression portions, or both on a surface thereof,
the structure layer comprises a polymerized product of an active energy ray curable resin composition;
the active energy ray curable resin composition comprises a composition of a (meth)acrylate-based polymerizable compound;
the composition of a (meth)acrylate-based polymerizable compound comprises at least any of the following (A) and (B), and the following (C) and (D):
 (A) an ester (meth)acrylate of a trihydric alcohol having a main chain and a side chain each comprising an alkyl chain;
 (B) an ester di(meth)acrylate of ethylene oxide-modified bisphenol A;
 (C) a polyalkylene glycol di(meth)acrylate; and
 (D) an ester di(meth)acrylate of a dihydric alcohol having a main chain comprising a linear alkyl chain;
a water contact angle on a surface of the structure layer is 26° or more and 74° or less; and
a storage elastic modulus at 180° C. of the structure layer is less than 0.5 GPa, when the structure layer has the protrusion portions, an average distance between the protrusion portions adjacent is equal to or less than a wavelength of visible light, when the structure layer has the depression portions, an average distance between the depression portions adjacent is equal to or less than a wavelength of visible light, and when the structure layer has the protrusion portions and the depression portions, the average distance between the adjacent protrusion portions and the average distance between the adjacent depression portions is each equal to or less than a wavelength of visible light.

2. The transparent laminate according to claim 1, wherein the composition of a (meth)acrylate-based polymerizable compound comprises the (A), (B), (C) and (D).

3. The transparent laminate according to claim 1, wherein the composition of a (meth)acrylate-based polymerizable compound comprises the (A) or the (B), the (C), and the (D), and the water contact angle is 26° or more and 60° or less.

4. The transparent laminate according to claim 1, wherein the ester (meth)acrylate (A) of a trihydric alcohol having a main chain and a side chain each comprising an alkyl chain is trimethylolpropane triacrylate.

5. The transparent laminate according to claim 4, wherein a content of the trimethylolpropane triacrylate in the composition of a (meth)acrylate-based polymerizable compound is less than 24.8% by mass.

6. The transparent laminate according to claim 1, wherein the polyalkylene glycol di(meth)acrylate (C) contains polyethylene glycol diacrylate having more than 8 ethylene oxide (EO) chain repeating units.

7. The transparent laminate according to claim 1, wherein a tensile elongation at break of the structure layer is 0.65% or more.

8. The transparent laminate according to claim 1, for use as a face protective optical element.

* * * * *